Figure 1:
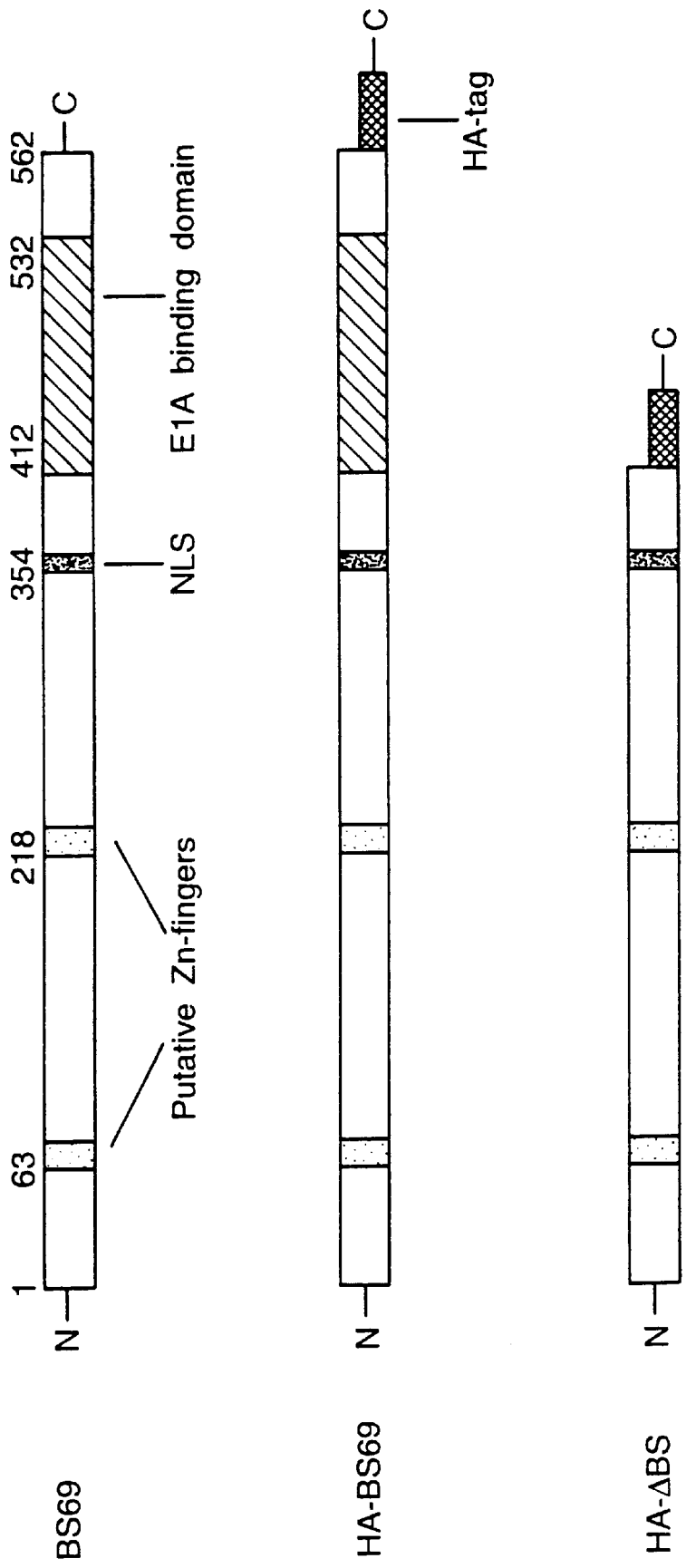

United States Patent [19]
Hateboer et al.

[11] Patent Number: 5,985,283
[45] Date of Patent: Nov. 16, 1999

[54] ADENOVIRUS E1A-ASSOCIATED PROTEIN BS69, INHIBITOR OF E1A-TRANSACTIVATION

[75] Inventors: Guus Hateboer; René Bernards, both of Amsterdam, Netherlands

[73] Assignee: Prolifix Limited, Abingdon, United Kingdom

[21] Appl. No.: 08/973,675

[22] PCT Filed: Jun. 14, 1996

[86] PCT No.: PCT/GB96/01413

§ 371 Date: Dec. 12, 1997

§ 102(e) Date: Dec. 12, 1997

[87] PCT Pub. No.: WO97/00323

PCT Pub. Date: Jan. 3, 1997

[30] Foreign Application Priority Data

Jun. 14, 1995 [GB] United Kingdom .................... 9512092

[51] Int. Cl.[6] .......................... A61K 39/23; A61K 39/12; C12N 7/00; C12N 15/00
[52] U.S. Cl. .................................. 424/233.1; 424/186.1; 424/199.1; 424/204.1; 536/23.72; 536/23.5; 435/235.1; 435/320.1; 435/5; 435/6
[58] Field of Search ................................. 435/5, 320.1, 6, 435/235.1; 424/199.1, 186.1, 233.1, 204.1; 536/23.72, 23.5

[56] References Cited

PUBLICATIONS

EMBO Journal, vol. 14, No. 13, Jul. 3, 1995, Eynsham, Oxford GB, pp. 3159–3169, XP000579801 Hateboer, R. et al.: "BS69, a novel adenovirus E1A–associated protein that inhibits E1A transactivation" see the whole document.

Nature Genetics, vol. 4, 1993, pp. 373–380, XP000600257 Adams, M.D. et al.: "Rapid cDNA sequencing (expressed sequence tags) from a directionally cloned human infant brain cNDA library" see table 1 & EMBL EST6, Accession No. T08073, sequence reference EST05964, Aug.–05–1993 Homo sapiens cNDA clone HIBAB61 5'end.

Comptes Rendus Des Seances De L'Academie Des Sciences Serie III: Sciences De La Vie., vol. 318, 1995, Montreuil FR, pp. 263–272, XP000579830 Aufray, C. et al.: "Image: integrated molegular analysis of the human genome and its expression" see the whole document & EMBL EST5, Accession No. Z44907, Sequence reference Hsc2ce021, Nov.–06–1994, H. Sapiens partial cDNA sequence; clone c–2ce02.

Proceedings of the National Academy of Sciences of USA, vol. 90, No. 18, 1993, Washington US, pp. 8489–8493, XP000579826 Hateboer, G. et al.: "TATA–binding protein and the retinoblastoma gene product bind to overlapping epitopes on c–myc and adnovirus E1A protein" see the whole document.

Egan et al. 1987, Virology, vol. 160, pp. 292–296, 1987.

*Primary Examiner*—Chris Eisenschenk
*Assistant Examiner*—Ali R. Salimi
*Attorney, Agent, or Firm*—Nixon & Vanderhye P.C.

[57] ABSTRACT

The present invention relates to a transcription inhibiting factor, designated BS69. The factor can bind to both the 243R and 289R E1A adenovirus proteins, inhibiting the transactivating activity of the latter.

12 Claims, 3 Drawing Sheets

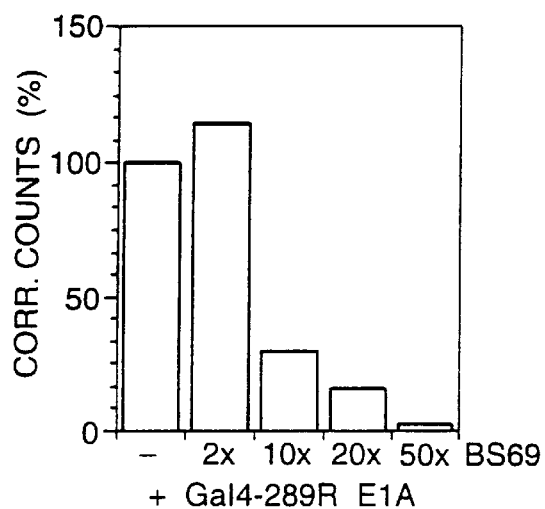
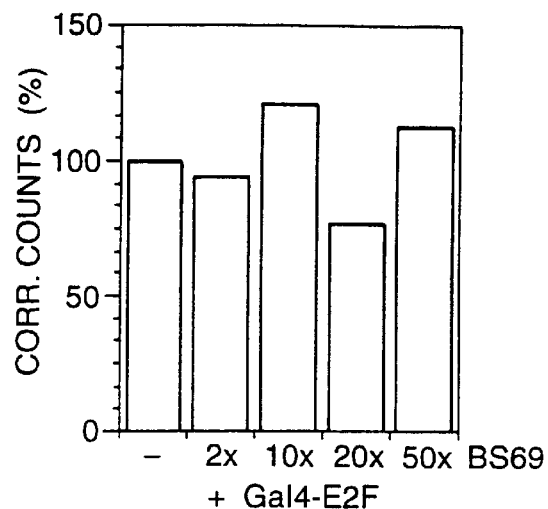
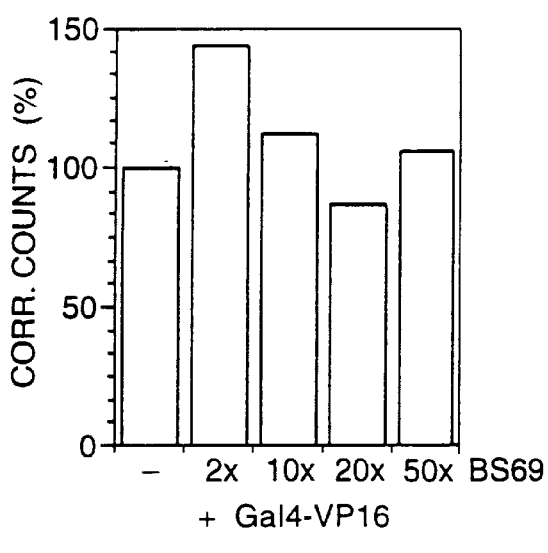
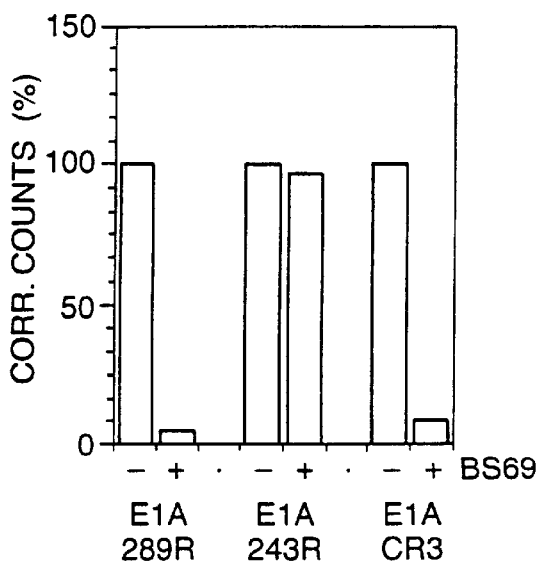

ADENOVIRUS E1A-ASSOCIATED PROTEIN BS69, INHIBITOR OF E1A-TRANSACTIVATION

This is a Rule 371 application based on the priority date of PCT/GB96/01413, filed Jun. 14, 1996.

This invention relates to a novel suppressor of transactivation.

In particular, the invention relates to BS69, a novel adenovirus E1A-associated protein which inhibits E1A transactivation. This protein can bind to the known viral transcription factors, adenovirus E1A, and can thus suppress the ability of the E1A factors to activate transcription. Hence BS69 can inhibit viral replication and may find use as an anti-adenoviral agent.

The adenovirus E1A gene products are nuclear phosphoproteins that can transactivate other adenovirus early genes as well as several cellular genes, and can transform primary rodent cells in culture. Transformation and transactivation by E1A proteins is most likely mediated through binding to several cellular proteins including the retinoblastoma gene product pRb, the pRb-related p107 and p130, and the TATA box binding protein TBP.

In transformed cells, early region 1A (E1A) of human adenoviruses encode two mRNAs that specify proteins of 243 and 289 amino acids respectively (243R and 289R E1A). E1A proteins can transform primary rodent cells in culture (Houweling et al., 1980) and they stimulate the expression of other early viral genes (Jones and Shenk, 1979) and some cellular genes (Shenk and Flint, 1991). E1A proteins of different serotypes share three regions of significant homology (conserved region (CR) 1, 2 and 3, Lillie et al., 1987). The 243R and the 289R E1A proteins share CR1 and 2, while CR3 is unique in the 289R E1A. CR3 consists of 46 amino acids and specifies a strong transactivation domain (Martin et al., 1990; Green et al., 1988; Lillie and Green, 1989). Activation of gene expression was also detected by the 243R E1A protein (Simon et al., 1987) and by domains encoded by exon 2 of Ad5 E1A (Myrnryk and Bayley, 1993). CR1 and 2 are involved in transformation (Lillie et al., 1987; Whyte et al., 1989), suppression of enhancer activity (Borelli et al., 1984; Velcich and Ziff, 1985; Wang et al., 1993) and the induction of DNA synthesis (Howe and Bayley, 1992; Lillie et al., 1987; Wang et al., 1991).

CR1 and CR2 are thought to exert their effect on cellular physiology by interacting with a number of cellular proteins (Barbeau et al., 1994; Egan et al., 1987; Harlow et al., 1986; Yee and Branton, 1985). Several of these cellular E1A-binding proteins have now been identified. They include the retinoblastoma gene product pRb (Whyte et al., 1988), the pRb-like proteins p107 (Whyte et al., 1989; Zhu et al., 1993) and p130 cannon et al., 1993; Li et al., 1993), cyclin A (Pines and Hunter, 1990) and p300 (Eckner et al., 1994). However, several additional cellular polypeptides have been identified in E1A immunoprecipitates of adenovirus-transformed or adenovirus-infected cells. They include proteins of 30, 33, 75, 95, 150, 180 and >250 kDa molecular weight (Egan et al., 1987). Since several of the presently identified E1A-interacting proteins play important roles in either cell cycle control or transcriptional regulation, the isolation of additional E1A-interacting cDNAs could be of considerable interest.

E1A can transactivate by several distinct mechanisms. First, E1A can activate adenovirus early region 2 (E2) transcription by dissociation of the E2F transcription factor from pRb, thereby activating E2F (Bagchi et al., 1990; Bandara and La Thangue, 1991). It is likely that E1A can also activate the expression of several cellular genes by competing pRb, p107 or p130 from inactive E2F complexes (Bagchi et al., 1990). This activity requires conserved regions 1 and 2 of E1A and is independent of the activation domain that is specified by CR3 (Moran et al., 1986). Secondly, E1A can be recruited to promoters through direct binding to sequence-specific DNA binding proteins. For example, E1A can bind directly to the ATF2 transcription factor, which recruits E1A to the E3 promoter (Liu and Green, 1990, 1994; Maguire et al., 1991). Finally, the large (289R) E1A protein as well as a number of other transcriptional activators like VP16 and c-Myc, have been shown to bind directly to the TATA binding protein TBP through their transactivation domain (Geisberg et al., 1994; Hateboer et al., 1993; Horikoshi et al., 1991; Lee et al., 1991; Stringer et al., 1990). This provides a possible mechanistic explanation for the activity of transcriptional activators like VP16, c-Myc and E1A.

While E2F-1, a known transactivation factor, binds to DNA in its transactivating role, the E1A proteins do not, but instead interact with a protein already bound to DNA. Thus while the E1A proteins are properly described as transactivators, their role in this process may perhaps be more accurately described as transactivation co-activators.

Although the activation of transcription by many transcription factors is well documented, not much is known about suppression of transactivation. A well-studied model for transcriptional repression is the interaction of the retinoblastoma family of related proteins with the transcription factor E2F Interaction of pRb with E2F-1 and interaction of p107 with E2F-4 leads to suppression of E2F-mediated transactivation as a result of direct binding of the pRb(-like) protein to the E2F transactivation domain (Bagchi et al., 1990; Beijersbergen et al., 1994a). Moreover, p107 can suppress c-Myc transactivation (Beijersbergen et al. 1994b) and similarly, binding of the MDM2 protein to the p53 transactivation domain results in suppression of p53-mediated transactivation (Morand et al., 1992; Oliner et al., 1993).

Imperiale et al. (1984) have shown that embryonic carcinoma (EC) cells contain an activity that can substitute for E1A in lytic viral infection: the E1A-like activity (E1A-LA). In EC cells TBP and the retinoic acid receptor (RAR) functionally cooperate in transactivation of the RARb2 promoter in a strictly RA-dependent manner (Berkenstam et al., 1992). Such cooperativity is not observed in COS-7 cells, where RAR-dependent transcription from the RARb2 promoter is low. Significantly, in COS-7 cells E1A can stimulate RAR dependent transcription, suggesting that E1A substitute for the activity that is present in EC cells (Berkenstam et al., 1992, Keaveney et al., 1993).

The present invention derives from identification of an additional cellular protein that interact with adenovirus E1A. Unexpectedly a new transactivation inhibitor has been found which has been labelled BS69. The cDNA sequence and amino acid sequence of this protein is presented here as Seq. ID No. 1. This new protein will be referred to as BS69 throughout this specification.

The cDNA sequence of BS69 has in-frame stopcodons at positions 21–23 and 1836–1838. The putative nuclear localization signal is found at residues 354 to 360 (R to R). Cysteine residues forming two putative Zinc-finger motifs are found at residues 63, 66, 75, 78, 218, 221, 234 & 237. The E1A-binding epitope is found at residues 412 to 532.

In making of the invention a radioactively labelled E1A protein probe was used to screen a phage cDNA expression library. This allowed the cloning of BS69, a novel protein that specifically interacts with adenovirus 5 E1A.

BS69 has been found to have no significant homology to known proteins and requires the region that is unique to the large (289R) E1A protein for high affinity binding. BS69 and E1A proteins co-immunoprecipitate in adenovirus-transformed 293 cells, indicating that these proteins also interact in vivo. BS69 also specifically inhibits transactivation by the 289R E1A protein, but not by the 243R E1A protein. In addition BS69 suppressed the E1A-stimulated transcription of the retinoic acid receptor in COS cells, but did not affect the cellular E1A-like activity that is present in embryonic carcinoma cells. This indicates that BS69 is a specific suppressor of E1A-activated transcription. Thus the invention in a first aspect provides a protein as shown in Seq. ID No. 1, homologues thereof, and fragments of the sequence and their homologues, which can inhibit or suppress a mammalian transcription factor. In particular, the invention provides a polypeptide (preferably in substantially isolated form) comprising:

(a) BS69;

(b) the protein of Seq. ID No. 1;

(c) a mutant, allelic variant or species homologue of (a) or (b);

(d) a protein at least 70% homologous to (a) or (b);

(e) a polypeptide of (c) or (d) or a fragment of any one of (a) to (d) capable of binding to 243R or 289R and/or inhibiting the transactivation activity of 289R; or (f) a fragment of any of (a) to (e) of at least 15 amino acids long.

All polypeptides within this definition are referred to below as polypeptide(s) according to the invention.

The proteins 243R and 289R (E1A proteins) are referred to herein as complexing proteins or "complexors" (of BS69) as they may form a complex with the proteins of the invention. The proteins of the invention may interact or bind more strongly to 289R than 243R, and usually do not interact or bind with VP16 or E2F-1.

The terms "243R" and "289R", when used in relation to complexors or being able to bind or interact with the proteins of the invention, additionally include mutants, allelic variants or species homologues that are also capable of complexing with the proteins of the invention (or binding or interacting with them). In this regard mutants specifically contemplated are deletion mutants. In particular the following deletion mutants are envisaged:

(a) 1–185 of 289R;

(b) 76–243 of 243R; and (c) 1–120, 1–140 and 76–289 of 289R.

Mutants that have been made but are not included within this definition (they do not bind to BS69) are as follows:

(a) 1–49, 1–75 and 1–85 (of either 243R of 289R, these sequences in both proteins are identical); and (b) 185–289 of 289R.

A polypeptide of the invention will be in substantially isolated form it is free of other polypeptides with which it may be associated in its natural environment (eg in the body). It will be understood that the polypeptide may be mixed with carriers or diluents which will not interfere with the intended purpose of the polypeptide and yet still be regarded as substantially isolated.

The polypeptide of the invention may also be in a substantially purified form, in which case it will generally comprise the polypeptide in a preparation in which more than 90%, eg. 95%, 98% or 99% of the polypeptide in the preparation is a polypeptide of the invention.

Mutant polypeptides will possess one or more mutations which are additions, deletions, or substitutions of amino acid residues. Preferably the mutations will not affect, or at least not substantially the structure and/or function and/or properties of the polypeptide. Thus, mutants will suitably possess the ability to be able to bind with the E1A proteins, 243R and/or 289R. Mutants can either be naturally occurring (that is to say, purified or isolated from a natural source) or synthetic (for example, by performing site-directed mutagenesis on the encoding DNA). It will thus be apparent that polypeptides of the invention can be either naturally occurring or recombinant (that is to say prepared using genetic engineering techniques).

In the invention deletion mutants are particularly preferred. These may include:

(a) 1–411 of BS69, where the 150 amino acid carboxy terminus has been removed (referred to later as ΔBS); and (b) 412–532, the E1A binding domain.

An allelic variant will be a variant which will occur naturally in a human or mammalian (eg. murine) animal and which will function to regulate gene expression in a substantially similar manner to the protein in Seq. ID No. 1.

Similarly, a species homologue of the protein will be the equivalent protein which occurs naturally in another species, and which performs the equivalent function in that species to the protein of Seq. ID No. 1. Within any one species, a homologue may exist as several allelic variants, and these will all be considered homologues of the protein. Allelic variants and species homologues can be obtained by following the procedures described herein for the production of the protein of Seq. ID No. 1 and performing such procedures on a suitable cell source, eg from human or a rodent, carrying an allelic variant or another species. Since the protein may be evolutionarily conserved it will also be possible to use a polynucleotide of the invention to probe libraries made from human, rodent or other cells in order to obtain clones encoding the allelic or species variants. The clones can be manipulated by conventional techniques to identify a polypeptide of the invention which can then be produced by recombinant or synthetic techniques known per se. Preferred species homologues include mammalian or amphibian species homologues.

A protein at least 70% homologous to that in Seq. ID No. 1 is included in the invention, as are proteins at least 80 or 90% and more preferably at least 95% homologous to the protein shown in this listing. This will generally be over a region of at least 20, preferably at least 30, for instance at least 40, 60 or 100 or more contiguous amino acids. Methods of measuring protein homology are well known in the art and it will be understood by those of skill in the art that in the present context. Homology is usually calculated on the basis of amino acid identity (sometimes referred to as "hard homology").

Generally, fragments of the polypeptide in Seq. ID No. 1 or its allelic variants or species homologues thereof capable of forming a complex with the complexors will be at least 10, preferably at least 15, for example at least 20, 25, 30, 40, 50 or 60 amino acids in length.

It will be possible to determine whether fragments form a complex by providing the complexor protein and the fragment under conditions in which they normally form a trans-activating transcription factor, and determining whether or not a complex has formed. The determination may be made by, for example, measuring the ability of the complex to bind E1A in vitro, or alternatively determining the molecular weight of the putative complex by methods such as by glycerol gradients, centrifugation or size fractionation.

Preferred fragments include those which are capable of forming a trans-activation complex with E1A or other complexors. The examples herein describe a number of methods to analyse the function of the protein and these may be adapted to assess whether or not a polypeptide is capable of forming a complex with an E1A protein. For example, the polypeptide can be added to the complexor in the presence of a reporter gene construct adapted to be activated by E1A. Such an experiment can determine whether the polypeptide fragment has the necessary activity.

Human BS69 has been found to bind to two regions of the 289R protein; firstly the region 76–120 which lies between the CR1 and CR2 domains, and secondly the CR3 domain. As 243R does not possess the CR3 domain (which is responsible for transactivation) BS69 only binds to it in the 76–120 region mentioned. Therefore "complexors" in this specification (of BS69) include proteins that comprise the 76–120 region (of either 243R or 289R) and/or the CR3 region, or a mutant or homologue thereof that is capable of binding, and hence forming a complex with, BS69.

It has been found that neither VP16 or E2F-1 bind to BS69 and so these two proteins are not included within the definition of complexors.

A polypeptide of the invention may be labelled with a revealing or detectable label. The (revealing) label may be any suitable label which allows the polypeptide to be detected. Suitable labels include radioisotopes, e.g. $^{125}$I, enzymes, antibodies and linkers such as biotin. Labelled polypeptides of the invention may be used in diagnostic procedures such as immunoassays in order to determine the amount of a BS69 complexor in a sample.

A polypeptide or labelled polypeptide according to the invention may also be fixed to a solid phase, for example the wall of an immunoassay dish.

A second aspect of the invention relates to a polynucleotide which comprises:

(a) a sequence of nucleotides shown in Seq. ID No. 1;
(b) a sequence complementary to (a);
(c) a sequence capable of selectively hybridising to a sequence in either (a) or (b);
(d) a sequence encoding a polypeptide as defined in the first aspect; or (e) a fragment of any of the sequences in (a) to (d).

The present invention thus provides a polynucleotide, suitably in substantially isolated or purified form, which comprises a contiguous sequence of nucleotides which is capable of selectively hybridizing to the sequence of Seq. ID No. 1 or to a complementary sequence. Fragments will preferably be at least 45 bases in length.

Polynucleotides of the invention include the DNA sequence shown in Seq. ID No. 1 and fragments thereof capable of selectively hybridizing to the sequence of Seq. ID No. 1. A further embodiment of the invention provides a DNA coding for the protein in Seq. ID No. 1 or a fragment thereof.

The polynucleotide may also comprise RNA. It may also be a polynucleotide which includes within it synthetic or modified nucleotides. A number of different types of modification to oligonucleotides are known in the art. These include methylphosphonate and phosphorothionate backbones, addition of acridine or polylysine chains at the 3' and/or 5' ends of the molecule. For the purposes of the present invention, it is to be understood that the oligonucleotides described herein may be modified by any method available in the art. Such modifications may be carried out in order to enhance the in vivo activity or lifespan of oligonucleotides of the invention used in methods of therapy.

A polynucleotide capable of selectively hybridizing to the DNA of Seq. ID No. 1 will be generally at least 70%, preferably at least 80 or 90% and optimally at least 95% homologous to the DNA of Seq. ID No. 1 over a region of at least 20, preferably at least 30, for instance at least 40, 60 or 100 or more contiguous nucleotides. These polynucleotides are also within the invention.

A polynucleotide of the invention will be in substantially isolated form if it is in a form in which it is free of other polynucleotides with which it may be associated in its natural environment (usually the body). It will be understood that the polynucleotide may be mixed with carriers or diluents which will not interfere with the intended purpose of the polynucleotide and it may still be regarded as substantially isolated.

A polynucleotide according to the invention may be used to produce a primer, e.g. a PCR primer, a probe e.g. labelled with a revealing or detectable label by conventional means using radioactive or non-radioactive labels, or the polynucleotide may be cloned into a vector. Such primers, probes and other fragments of the DNA of Seq. ID No. 1 will be at least 15, preferably at least 20, for example at least 25, 30 or 40 nucleotides in length, and are also encompassed within the invention.

Polynucleotides, such as a DNA polynucleotides, according to the invention may be produced recombinantly, synthetically, or by any means available to those of skill in the art. It may be also cloned by reference to the techniques disclosed herein.

The invention includes a double stranded polynucleotide comprising a polynucleotide according to the invention and its complement.

A third aspect of the invention relates to an (eg. expression) vector suitable for the replication and expression of a polynucleotide, in particular a DNA or RNA polynucleotide, according to the invention. The vectors may be, for example, plasmid, virus or phage vectors provided with an origin of replication, optionally a promoter for the expression of the polynucleotide and optionally a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA or used to transfect or transform a host cell. The vector may also be adapted to be used in vivo, for example in a method of gene therapy.

Vectors of the third aspect are preferably recombinant replicable vectors. The vector may thus be used to replicate the DNA. Preferably, the DNA in the vector is operably linked to a control sequence which is capable of providing for the expression of the coding sequence by a host cell. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences. Such vectors may be transformed or transfected into a suitable host cell to provide for expression of a polypeptide of the invention.

A fourth aspect of the invention thus relates to host cells transformed or transfected with the vectors of the third aspect. This may allow for the replication and expression of a polynucleotide according to the invention, including the sequence of Seq. ID No. 1 or the open reading frame thereof. The cells will be chosen to be compatible with the vector and may for example be bacterial, yeast, insect or mammalian. Cells specifically contemplated include NIH3T3, COS-7, RAC65 and U2-OS cells.

Thus, in a fifth aspect the invention provides a process for preparing a polypeptide according to the invention which comprises cultivating a host cell transformed or transfected with an (expression) vector of the third aspect under conditions providing for expression (by the vector) of a coding sequence encoding the polypeptide, and recovering the expressed polypeptide.

The invention in a sixth aspect also provides (monoclonal or polyclonal) antibodies specific for a polypeptide according to the invention. Antibodies of the invention include fragments, thereof as well as mutants that retain the antibody's binding activity. The invention further provides a process for the production of monoclonal or polyclonal antibodies to a polypeptide of the invention. Monoclonal antibodies may be prepared by conventional hybridoma technology using the proteins or peptide fragments thereof as an immunogen. Polyclonal antibodies may also be prepared by conventional means which comprise inoculating a host animal, for example a rat or a rabbit, with a polypeptide of the invention and recovering immune serum.

Fragments of monoclonal antibodies which can retain their antigen binding activity, such Fv, F(ab') and F(ab$_2$)' fragments are included in this aspect of the invention. In addition, monoclonal antibodies according to the invention may be analyzed (eg. by DNA sequence analysis of the genes expressing such antibodies) and humanized antibody with complementarity determining regions of an antibody according to the invention may be made, for example in accordance with the methods disclosed in EP-A-0239400 (Winter).

The present invention in a seventh aspect further provides compositions comprising the antibody or fragment thereof of the invention together with a carrier or diluent.

Polypeptides of the invention can be present in addition to, or instead of, the antibodies of the invention in such compositions together with a carrier or diluent. Compositions of this aspect include pharmaceutical compositions where the carrier or diluent will be pharmaceutically acceptable.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostatis and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

In an eighth aspect polypeptides according to the invention, antibodies or fragments thereof to polypeptides according to the invention and the above-mentioned compositions may be used for the treatment, regulation or diagnosis of conditions, including proliferative diseases, in mammals, including man. Such conditions include those associated with abnormal (eg at an unusually high or low level) and/or aberrant (eg due to a mutation in the gene sequence) expression of one or more factors such as the BS69 or E1A proteins or related family members. The conditions also include those which are brought about by abnormal expression of a gene whose gene product is regulated by the protein of Seq. ID No. 1. Treatment or regulation of conditions with the above-mentioned peptides, antibodies, fragments thereof and compositions etc. will usually involve administering to a recipient in need of such treatment an effective amount of a polypeptide, antibody, fragment thereof or composition, as appropriate.

The invention also provides antibodies, and fragments thereof, targeted to this region in order to modulate the activation of transcription factors via the disruption of the formation of the complex between BS69 (or a polypeptide of the invention) and a complexor.

Thus this aspect of the invention specifically contemplates the use of the polypeptides of the invention for use in medicine, or, more specifically, in methods of treatment of the human or animal body by therapy or diagnostic methods practised on the human or animal body.

A ninth aspect of the invention relates to the use of a polypeptide of the first aspect in the manufacture of a medicament for treating a viral mediated disease or disorder. Thus the polypeptides can be used to treat viral infections, and may thus act as an antiviral agent. In particular this aspect contemplates adenoviruses (eg. Ad5) and hence envisages treating any adenovirus mediated or induced disorder. In particular polypeptides of the invention that inhibit, prevent, repress or suppress E1A function and/or E1A transactivation are embraced within this aspect.

The present invention further provides a method of performing an immunoassay for detecting the presence or absence of a polypeptide of the invention in a sample, the method comprising:

(a) providing an antibody according to the invention;

(b) incubating the sample with the antibody under conditions that allow for the formation of an antibody-antigen complex; and (c) detecting, if present, the antibody-antigen complex.

In another aspect, the invention provides a novel assay for identifying putative chemotherapeutic agents for the treatment of viral disease which comprises bringing into contact an E1A protein (or a derivative thereof), a polypeptide of the invention and a putative chemotherapeutic agent, and measuring the degree of inhibition of formation of the protein/E1A protein complex caused by the agent. It may not be necessary to use complete BS69 and/or E1A protein in the assay, as long as sufficient of each protein is provided such that under the conditions of the assay in the absence of agent, they form a heterodimer.

Thus, the invention provides a screening method for identifying a putative chemotherapeutic agent capable of inhibiting or suppressing transactivation or for the treatment of a viral disease, which comprises:

(A) bringing into contact:

(i) an E1A protein or complexor of BS69;

(ii) a polypeptide of the first aspect; and (iii) a putative chemotherapeutic agent;

under conditions in which the components (i) and (ii) in the absence of (iii) form a complex; and (B) measuring the extent to which component (iii) is able to disrupt the complex and/or inhibit or suppress transactivation.

In the assay, any one or more of the three components may be labelled, eg with a radioactive or calorimetric label, to allow measurement of the result of the assay. Putative chemotherapeutic agents include peptides of the invention.

Variants, homologues and fragments of E1A proteins are defined in a corresponding manner to the variants, homologues and fragments of the polypeptides of the invention.

The complex of (i) and (ii) may be measured, for example, by the reduced ability of E1A to perofrm transactivation. Alternatively, the assay may be an in vivo assay in which the ability of the complex to activate a promoter comprising a DNA binding site linked to a reporter gene (eg. GAL4) is measured. The in vivo assay may be performed for example by reference to the examples which show such an assay in yeast, insect, amphibian or mammalian cells.

Candidate therapeutic agents which may be measured by the assay include not only polypeptides of the first aspect, but in particular fragments of 10 or more amino acids of:

(a) the protein of Seq. ID No. 1;

(b) an allelic variant or species homologue thereof; or (c) a protein at least 70% homologous to (a).

An additional assay that can be performed can screen for potential transactivation or transcription agents, by:

(a) bringing into contact a polypeptide of the invention and the agent; and (b) determining whether the polypeptide and agent bind together, or form a complex; and (c) optionally determining the extent of (eg. reduced) transactivation activity of the agent.

A further assay for potential transactivation inhibiting or suppressing agents involves:

(a) bringing into contact a protein which is 243R, 289R or a complexor of BS69 with the agent;

(b) determining whether the protein and agent bind together, or form a complex; and (c) optionally determining the extent to which the agent is able to inhibit or suppress transactivation activity.

Vectors carrying a polynucleotide according to the invention or a nucleic acid encoding a polypeptide according to the invention may be used in a method of gene therapy. Such gene therapy may be used to treat uncontrolled proliferation of cells, for example a tumour cell. Methods of gene therapy include delivering to a cell in a patient in need of treatment an effective amount of a vector capable of expressing in the cell a polynucleotide of the invention in order to inhibit, or reduce the translation of BS69 mRNA.

The vector is suitably a viral vector. The viral vector may be any suitable vector available in the art for targeting tumour cells. For example, Huber et al (Proc. Natl. Acac. Sci. USA (1991) 88, 8039) report the use of amphotrophic retroviruses for the transformation of hepatoma, breast, colon or skin cells. Culver et al (Science (1992) 256; 1550–1552) also describe the use of retroviral vectors in virus-directed enzyme prodrug therapy, as do Ram et al (Cancer Research (1993) 53; 83–88). Englehardt et al (Nature Genetics (1993) 4; 27–34 describe the use of adenovirus based vectors in the delivery of the cystic fibrosis transmembrane conductance product (CFTR) into cells.

The invention contemplates a number of assays. Broadly, these can be classified as follows.

1. Conducting an assay to find an inhibitor of E1A transactivation. This inhibitor may therefore bind to the E1A transactivation domain of E1A. Potentially suitable inhibitors are proteins, and may have a similar or same effect as BS69. Thus suitable inhibitory molecules may comprise fragments, mutants, allelic variants, or species homologues of BS69.

2. Assaying for promoters or inhibitors of (hetero) dimerisation. Such inhibitors may assist or prevent dimerisation of BS69 or a polypeptide of the first aspect with a complexor, for example an E1A protein, such as 289R.

3. Assaying for transcription factors using the proteins of the invention. DNA encoding these factors can be isolated by protein interaction cloning, such as yeast two-hybrid interaction screening or screening of cDNA expression libraries with a labelled polynucleotide of the invention.

The invention contemplates a number of therapeutic uses. For example, gene therapy using a polynucleotide of the invention. Molecules that can bind to an E1A protein and thereby suppress E1A activity are additionally contemplated. Suitable molecules include those of the first aspect apart from BS69 itself. The invention thus contemplates the treatment or prophylaxis of viral diseases.

The following Example describes the isolation and characterization of the novel protein and DNA of the invention from human and murine sources, respectively. However, other e.g. mammalian sources are within the scope of the present invention and other mammalian homologues of the protein may be isolated in an analogous manner. The Example is presented here by way of illustration and is not to be construed as limiting on the invention.

The Example makes reference to the accompanying drawings, in which:

FIG. 1 gives a schematic representation of human BS69. In detail, the figure shows schematic representation of BS69 and the constructs HA-BS69 and HA-ΔBS, used for transient transfections. The E1A binding domain is indicated with an hatched bar. The HA-tag, a 10 residue epitope recognized by the 12CA5 antibody was cloned in-frame downstream of the BS69 open reading frame. In the HA-ΔBS construct the C-terminal 150 amino acids spanning the putative E1A-binding domain was deleted and the HA-tag was cloned downstream of residue 411 of BS69. The ATG start site in both constructs was modified to fit a consensus translation start site.

FIG. 2 shows the specific repression by BS69 of E1A-mediated tansactivation.

(A) Concentration dependent repression by BS69 on E1A transcriptional activation.

(B) and (C) BS69 does not inhibit transactivation by GAL4-E2F1 and GAL4-VP16 in a concentration dependent manner.

(D) Repression of 289R E1A transactivation by BS69 is directed through CR3 in 289R E1A. 243R E1A transactivation is not repressed by BS69.

(E). A deletion mutant of BS69, lacking the putative E1A-binding epitope, HA-ΔBS, did not inhibit E1A-mediated transactivation, when a 6, 12 or 50 fold excess of plasmid was co-transfected with GAL4-E1A activator. Full-sized HA-BS69 inhibited, using the same amounts of plasmid. GAL4 alone does not activate the reporter and also a fusion between GAL4 and BS69 full length protein did not activate the reporter. All data are representative for at least three independent experiments. Percentages of conversion of the substrates in the lysates from cells transfected with the activators alone were for 289R E1A: 20%, for E2F: 14%, for VP16: 14%, CR3: 5% and for 243R E1A: 21% (averages over at least three independent experiments). Percentage of conversion of the background counts never exceeded 0.8%.

Luciferase counts were not significantly influenced by the presence of the activators in any of the experiments.

FIG. 3 shows the repression of E1A-stimulated transcription of the RARb2 promoter by BS69.

(A) COS-7 cells were transfected with expression vectors for human mutant TBP (TBP/spm3, 2.0 mg per dish), RAR (pSG-RARb2, 0.5 mg per dish) and 289R E1A (pBS 289R E1A, 1.0 mg per dish) as depicted. Amounts of HA-BS69 expression vector that was cotransfected were 1, 2.5 and 5 mg. All transfections contained EF1a-CAT (0.15 mg per dish) as an internal standard and M1-Luc (5.0 mg per dish) as the reporter plasmid comprising the RARb2 promoter.

(B) RAC65 cells containing the E1A-like activity were transfected with expression plasmids for TBP and RAR as in (A) as were the internal control and reporter plasmids. The amounts of cotransfected HA-BS69 expression plasmid were: 0.5, 2.5 and 5 mg. Data are representative for at least three independent experiments.

Reference may also be made to Hateboer et al, EMBO J 14; 3159–3169, 1995, published on Jun. 15, 1995, for further illustration of the Examples described herein.

EXAMPLE 1

Isolation and sequencing of human BS69 cDNA

The 289R E1A cDNA from Adenovirus 5 was cloned into pET15b (Novagen), upstream of six histidine codons and downstream of a sequence encoding a cAMP-dependent protein kinase phosphorylation site. The encoded protein was purified from *E. coli* over Ni-agarose and labelled in vitro with protein kinase (Sigma catalogue no. P-2645) and [$\gamma$-$^{32}$P]-ATP as described by Kaelin et al. (1992). The labelled protein was used to screen a 16-day whole mouse embryo cDNA expression library (EX1ox, Novagen) as has been described (Kaelin et al., 1992). A partial mouse cDNA was used to screen a T84 human colon carcinoma cDNA library to isolate a full length human BS69 cDNA. Both strands of the gene were sequenced completely using the Pharmacia T7 sequencing kit.

Plasmids

PCR was used to synthesize two BS69 clones, both with a consensus translation start site and a carboxyl terminal HA-tag, recognized by the 12CA5 antibody (Field et al., 1988). HA-BS69 contains the complete BS69 open reading frame, while HA-$\Delta$BS lacks the C-terminal 150 amino acids. Both PCR products were cloned into the HindIII and NotI sites of the mammalian expression vector pRc/CMV (Invitrogen).

For in vivo association experiments after transient expression the 289R E1A cDNA from adenovirus 5 in pRSV was used (kindly provided by A. G. Jochemsen). Only for the cotransfection experiment using HA-$\Delta$BS, an expression vector, p5Xhocc4, was used (Bernards et al., 1982), expressing both 243R and 289R E1A under the control of the E1A promoter. All GAL4-E1A fusions were cloned downstream of the DNA binding domain of the yeast transcription factor GAL4 (aa 1–147) in the mammalian expression vector pJ3. pSG-GAL4-E2F1 was kindly provided by K. Helin, pSG-GAL4-VP16 (Kato et al., 1990) was kindly provided by C. V. Dang. All GAL4 fusions used in these studies are driven by the SV40 promoter, except for GAL4-BS69 which is driven by the CMV promoter in pRc/CMV. Full length BS69 cDNA was cloned downstream of glutathione S-transferase (GST) in pVLGST (kindly provided by M. Gebbink) for recombination in baculovirus and in pGEX-2T for production in *E. coli*. pGEX-2T-HU contained residues 397–562 of BS69, cloned directly from the mouse cDNA identified in the expression library.

For in vitro transcription and translation the following constructs were used. Full length 243R and 289R E1A proteins were generated by using pCS-12S and pBS-13S respectively, both provided by E. Harlow. p107 protein was generated by using pGEM4-p107, provided by B. Smith-Sorensen. The partial mouse BS69 protein (from pBS2) was one of the three independent inserts that were identified in the expression screening, and it is a fusion with the T7 gene-10 product from pEX1ox (Novagen). For the mapping on E1A, 243R, 289R and several deletion mutants were generated by PCR and cloned downstream of the T7 gene-10 gene in pEX1ox for proper transcription and stabilization of the translated product. For the HA-tagged 289R E1A, carboxyl-terminal deletion mutant 189–289 and CR3 alone, PCR was performed and inserts were cloned downstream of the HA-epitope in pMV-1 (+1), provided by M. Voorhoeve. All constructs were checked for frameshifts and mutations, using the Pharmacia T7 sequencing kit.

For experiments on the E1A-dependent activation on the RARb2 promoter following plasmids were used: EF1a-CAT expression plasmid (Mizushima and Nagata. 1990), M1-Luc reporter (Keaveney et al., 1993), Human TBP/spm3 expression plasmid (Strubin and Struhl, 1992), pSG-RARb2 expression plasmid (Berkenstam et al., 1992) and pBS 289R E1A expression plasmid (Webster and Ricciardi, 1991).

Antibodies

Recombinant baculovirus was generated in Sf9 cells following the cotransfection procedure described by the supplier (PharminGen). 40% confluent plates containing Sf9 cells were infected with approximately 100 pfu of virus per cell. Two days post infection, cells were harvested and lysed by sonication in E1A lysis buffer (ELB, Harlow et al., 1986). GST-BS69 fusion protein was purified from the lysates using glutathione sepharose beads (Pharmacia). Beads carrying 100 mg fusion protein were used for immunization of rabbits.

GST-BS69 purified from *E. coli* was used to immunize and boost mice to obtain hybridomas producing monoclonal antibodies against BS69 protein. One hybridoma, RK115, was used in these studies.

Cell culture, transfections and labelling

Cells were maintained in Dulbecco's modified Eagle's medium (DMEM) supplemented with 10% fetal calf serum (FCS). Sf9 cells were maintained at 26° C. in Grace's insect medium (Invitrogen) supplemented with 10% FCS. Transfections were performed overnight using the calcium phosphate method. For methionine labelling, cells were starved for 1 hr in methionine-free medium and subsequently incubated with 100 mCi of [$^{35}$S]-methionine per 100 mm dish for 1 hr. After this, cells were lysed by sonication in ELB. Equal amounts of radioactive lysates were incubated on ice for 30 minutes with 5 ml non-immune serum (ni.) for preclearing. Subsequently, lysates were incubated for 1 hr with specific antibodies. For phosphate labelling, cells were starved for 1 hr in phosphate-free medium. After this, 2.5 mCi of [$^{32}$p]-orthophosphate was added to the transiently transfected cells and 20 mCi to the 293 cells for 4 hr. For sequential immunoprecipitations, first immunoprecipitations were boiled in 100 ml ELB supplemented with 2% SDS and 15mM DTT for 5 minutes. Released proteins were diluted 10-fold with ELB buffer and used for re-immunoprecipitation with either non immune serum or specific antibody. All immunoprecipitates were collected by binding to protein A-Sepharose, washed four times in ELB, heated in SDS containing sample buffer and loaded on a SDS/10% polyacrylamide gel.

NIH3T3 cells were stably transfected with 15 mg HA-BS69 expression vector per 100 mm dish. Neomycin resistant colonies were selected and checked for the expression of BS69 mRNA and protein. COS-7 and RAC65 cells were seeded 24 and 46 hrs, respectively, prior to transfection. Medium was changed 2 hrs before adding the precipitate. The total amount of DNA per dish was adjusted with empty vector (pSG) up to 13.65 mg (COS-7) and 12.65 mg (RAC65). 15 hrs after transfection the medium was changed and the cells were induced with retinoic acid (final concentration 1 mM).

Immunoblotting

Three 15 cm dishes of NIH3T3-B5 and CAMA cells were lysed by sonication in 2 ml RIPA buffer supplemented with protease inhibitors. Lysates were split and immunoprecipitations were performed with either 10 ml normal rabbit serum or 10 ml anti BS69 polyclonal rabbit serum for 3 hr on ice. Immunoprecipitates were collected by protein A-Sepharose, washed four times in RIPA and separated on a SDS/10% polyacrylamide gel. Transfer was performed overnight to nitrocellulose. Filter was blocked in PBS supplemented with 0.05% Tween-20 and 5% non-fat milk (Protifar, Nutricia) (TPBS, 5% milk) for 1 hr at RT, incubated with RK115 ascites in a dilution of 1:2000 in TPBS, 1% milk for 3 hr at RT, and incubated with secondary antibody in TPBS, 1% milk. Filter was washed 3 times in TPBS and visualization was performed by enhanced chemiluminescence (Amersham).

Northern blotting

Poly-A mRNA was selected from whole mouse tissues and transferred to Hybond-N filter. The blot was first hybridized with a partial mouse BS69 cDNA clone and subsequently probed with a partial cDNA from the rat tubulin gene to check for the amounts of mRNA loaded in each lane.

In vitro transcription, translation and binding assays

Proteins were made by in vitro transcription and translation of the cDNAs using rabbit reticulocyte lysates (Promega) and [$^{35}$S]-methionine. For in vitro binding assays, equal amounts of protein were mixed and incubated for 2 hr in 0.5 ml ELB on ice. 50 ml of hybridoma supernatant (M73) was added and precipitation was performed overnight on ice.

Immunoprecipitates were collected by binding to protein A-Sepharose for 1 hr at 4° C., washed four times in ELB, heated in SDS containing sample buffer and loaded on an SDS/10% polyacrylamide gel. For GST-pull down assays, equal amounts of protein were mixed with 1.0 mg GST-HII fusion protein and incubated for 2 hr in 0.5 ml ELB on ice. 50 ml Glutathion Sepharose beads (Pharmacia, 30% slurry) was added and rocked for 1 hr at 4° C. Beads were washed four times in ELB, heated in SDS sample buffer and loaded on an SDS/10% polyacrylamide gel. For the GST-pull down assay using HA-tagged 289R E1A, 189-289 deletion mutant and CR3, in vitro translated protein were mixed with 50 ml Glutathion Sepharose beads (30% slurry), covered with GST-BS69 fusion protein from baculovirus infected cells and incubated in 0.5 ml NETN (100 mM NaCi, 0.5% NP40, 50 mM Tris-HCl pH 7.0, 5 mM EDTA) at 4° C. while rocking overnight. Beads were washed four times in NETN, heated in SDS sample buffer and loaded on an SDS/20% polyacrylamide gel. To check for input and translation of the HA-tagged products, equal amounts of translations were incubated with 50 ml 12CA5 hybridoma supernatant in 0.5 ml ELB overnight at 4° C. Immunoprecipitates were collected by binding to protein A-Sepharose for 1 hr at 4° C., washed four times in ELB, heated in SDS containing sample buffer and loaded on the same SDS/20% polyacrylamide gel as the pulled down proteins.

CAT and Luciferase assays

U2-OS cells were transiently transfected in triplicate with 15 mg total DNA, using pRc/CMV empty vector as a carrier. Amounts of the HA-BS69 expression vector co-transfected with pJ3GAL4-289R E1A, were 500 ng (2×), 2.5 mg (10×), 5.0 mg (20×) and 12.5 mg (50×). For pSG-GAL4-E2F1 and pSGVP-GAL4-VP16, the amounts of HA-BS69 co-transfected, were 100 ng (2×). 250 ng (5×), 500 ng (10×) and 2.5 mg (50×). 1.0 mg of activators pJ3-GAL4-289R E1A, pJ3-GAL4-243R E1A and pJ3-GAL4-CR3 was either co-transfected with 12 mg empty vector or with 12 mg HA-BS69 expression vector. The amounts of pJ3-GAL4 and pRc/CMV-GAL4-BS69 were 5.0 mg plus 8.0 mg empty vector. The amounts of HA-ΔBS expression vector were 1.5 mg (6×), 3.0 mg (12×) and 12.5 mg (50×) over 250 ng activator (pJ3-GAL4-289R E1A). Equal amounts of HA-BS69 were used in this experiment as positive control of inhibition. Co-transfected in every dish were 0.2 mg of pRc/CMV luciferase reporter vector, to check for transfection efficiency, and 2.0 mg of the reporter construct harboring five GAL4 sites upstream of the E1B promoter and the Chloramphenicol Acetyl Transferase (CAT) gene. CAT activity was measured as described (Seed and Sheen, 1988). Luciferase activity was determined by scintillation counting (Promega, luciferase assay kit). Corrected counts were calculated by dividing the CAT counts by the luciferase counts, minus the background. The counts from the activators, not co-transfected with HA-BS69, were depicted as 100%. COS-7 and RAC65 were harvested 24 hrs post transfection and the extracts were used for luciferase and CAT assays. Luciferase activity was determined by scintillation counting and CAT values were measured by using the CAT ELISA Kit from Boehringer following the protocol provided by the manufacturer.

Cloning of adenovirus E1A associated BS69

A day 16 whole mouse embryo cDNA expression library was screened in IEX1ox with a [$^{32}$P]-labelled bacterially-synthesized 289R Ad5 E1A protein probe. Twelve recombinant phage were identified whose encoded proteins bound strongly to E1A protein. DNA sequence analysis of the cDNAs indicated that all phage were derived from the same gene. Three different size classes of inserts were found. A partial mouse cDNA was subsequently used to isolate a full length human cDNA from, a colon carcinoma cDNA library. Sequence analysis of the human cDNA indicates that it encodes a 562 amino acid protein with no significant homology to known genes. In vitro transcription and translation of the human cDNA showed that the molecular weight of the encoded protein is approximately 69 kDa. This novel protein was hence named BS69. There are two putative zinc finger motifs in the amino terminal part of BS69 and a potential nuclear localization signal (NLS) starting at position 354 (FIG. 1).

By using in vitro translated BS69 deletion mutants in a binding assay with 289R E1A fused to Glutathione S-Transferase (GST), it was found that the E1A-binding epitope of BS69 is located between amino acids 412 and 532. To study the effect of BS69 on E1A function two expression plasmids were constructed, one containing the full length BS69 cDNA (HA-BS69) and one lacking the E1A binding region (HA-ΔBS). Both inserts were cloned upstream from the fragment encoding the HA-epitope (Field et al., 1988).

Expression levels of BS69 in mouse tissues

To determine the expression pattern of BS69 we performed northern blot analysis using poly-A selected mRNA from several mouse tissues. Northern blot containing poly-A selected mRNA from total mouse tissues was probed with partial cDNA clones from mouse BS69 and rat tubulin genes. It was found that an approximate 4.7 kb BS69 transcript was expressed in all tissues tested. The highest level was found in kidney and lower levels in lung, brain, spleen, thymus and testis. As a control for the amount of mRNA present in each lane the northern blot was reprobed with a partial cDNA fragment from the rat tubulin gene.

BS69 has different affinities for 243R and 289R E1A proteins

To investigate which domain of E1A mediates binding to BS69, an in vitro binding assay was performed using in vitro transcribed and translated 243R and 289R E1A proteins and mixed these proteins with an in vitro translated carboxyl-terminal fragment of mouse BS69 protein. In vitro translated p107 was used as a control as this protein has equal affinity for both E1A proteins. Proteins bound to E1A were co-immunoprecipitated with the anti E1A monoclonal antibody M73. In vitro transcribed and translated 243R and 289R E1A protein were mixed with an in vitro transcribed and translated carboxyl-terminal fragment of mouse BS69 or human p107. Complexes were immunoprecipitated with the E1A specific monoclonal antibody M73. It was found that BS69 binds the 289R E1A species and, to a lesser extent, the 243R E1A protein whereas p107 interacted with both E1A proteins equally well. This result suggests that BS69 requires the 46 amino acid domain that is unique to the 289R E1A protein for high affinity binding.

Since 243R and 289R E1A have different affinities for BS69 the interacting domains on both E1A proteins was mapped. A number of in vitro translated E1A deletion mutants were used, each fused to the T7 gene-10 for proper in vitro transcription and translation, in a GST-pull down assay with a GST-BS69 fusion protein. In vitro transcribed and translated deletion mutants of E1A fused to the T7 gene-10 protein were pulled down by GST-HII, a bacterially produced fusion protein containing the E1A binding domain of mouse BS69. It was found that a peptide consisting of amino acids 1–120 of 243R E1A binds GST-BS69 whereas amino acids 1–85 did not. Since a peptide spanning amino acids 76–243 of E1A also binds BS69 it was concluded that the region in 243R E1A protein responsible for binding to BS69 maps to amino acids 76–120, located between CR1 and 2 of E1A. However, one cannot exclude the possibility that residues upstream of position 76 or downstream of 120 also contribute to the binding of 243R E1A protein to BS69. The finding that 289R E1A binds with higher affinity to BS69 than 243R E1A suggests that CR3 contributes to BS69 binding. To investigate this, a GST-pull down assay was also performed using GST-BS69 from baculovirus infected cells and an in vitro translated peptide that consisted of CR3 linked to the HA-epitope, which is recognized by the 12CA5 antibody (Field et al., 1988). The HA-CR3 fusion protein has an approximate molecular weight of 6.5 kDa. In vitro translated HA-tagged 289R E1A (both panels, lane 1), HA-tagged carboxyl-terminal E1A mutant (consisting of amino acids 189–289) and HA-tagged CR3 were pulled down by GST-BS69 from Baculovirus and immunoprecipitated with 12CA5 antibody. Equal amounts of protein were used in both experiments. It was found that both HA-289R E1A and HA-CR3 are able to interact with GST-BS69 whereas the HA-tagged carboxyl-terminal residues 189–289 of E1A did not interact. To check for the input of translated proteins immunoprecipitations were performed on the three in vitro translated proteins using 12CA5 antibody. From these mapping experiments one can conclude that BS69 has two separate interaction domains on E1A, one located between CR1 and CR2 (aa. 76–120) and one in CR3, the region that is unique to the 289R E1A protein.

BS69 interacts with E1A in vivo

To investigate whether BS69 and E1A proteins also interact in vivo, the coding region of BS69 was cloned upstream of the HA-epitope in a mammalian expression vector (FIG. 1). Also constructed a deletion mutant of BS69, HA-ΔBS, lacking the putative E1A binding region (FIG. 1). Direct immunoprecipitations with E1A and HA-tag specific antibodies after [$^{35}$S]-methionine labelling of U2-OS cells, transfected with 289R E1A and HA-tagged BS69 (HABS69) alone or cotransfected with both expression vectors were performed. Cells transfected with 289R E1A alone were used for immunoprecipitation with the E1A specific monoclonal antibody M73 or with the HA-tag specific monoclonal antibody 12CA5. Cells transfected with BS69 alone were used for immunoprecipitation with M73 and with 12CA5 and cells cotransfected with both expression vectors were used for immunoprecipitation with M73 and with 12CA5. It was found that the E1A and BS69 proteins are expressed following transient transfection in the human osteosarcoma cell line U2-OS. Significantly, following co-transfection of BS69 and E1A expression vectors, a protein of 69 kDa, that co-migrates with BS69, was co-immunoprecipitated with E1A. The 12CA5 antibody does not recognize the E1A protein directly and the M73 antibody, directed against E1A, does not recognize BS69 directly. To verify that the 69 kDa E1A-associated protein was indeed BS69 a sequential immunoprecipitation experiment was performed. U2-OS cells were transiently transfected with E1A and BS69 expression vectors. After two days, cells were labelled with [$^{35}$S]-methionine and non-ionic detergent lysates were subjected to immunoprecipitation with either non immune (ni) mouse serum or M73 antibody. Proteins that co-immunoprecipitated with E1A were released by boiling in SDS-containing buffer, diluted, and subjected to re-immunoprecipitation with either non immune serum or 12CA5 antibody directed against HA-tagged BS69. It was found that when M73 was used as a first antibody and 12CA5 in a re-immunoprecipitation, a protein of 69 kDa was specifically immunoprecipitated. These data show that BS69 and E1A form a complex in transiently transfected cells.

When BS69 and 289R E1A expression vectors were transfected and 12CAS used for immunoprecipitation of HA-tagged BS69, only very small amounts of E1A co-immunoprecipitated with BS69. This may be due to the fact that the E1A-interaction domain is juxtaposed to the HA epitope, resulting in steric hindrance (FIG. 1). Since E1A proteins are highly phosphorylated, the experiment described above was repeated following a [$^{32}$P]-orthophosphate labelling of transiently transfected U2-OS cells. It was found that when 12CA5 was used as the first antibody and M73 for re-immunoprecipitation, one could detect the 289R E1A protein in the BS69 immunoprecipitation.

Using in vitro binding assays the interaction domain of E1A between amino acid 412 and 532 of BS69 was mapped. To investigate whether a deletion mutant lacking this region interacts with E1A in vivo, an expression vector encoding a mutant BS69 was constructed consisting of amino acids 1–41 1, linked to a downstream HA tag, named HA-ΔBS (FIG. 1). Direct immunoprecipitations were performed with E1A and HA-tag specific antibodies after [$^{35}$S]-methionine labelling of U2-OS cells, transfected with p5Xhocc4, encoding 243R and 289R E1A proteins and an expression vector encoding HA-tagged ABS (HA-ΔBS). Mock transfected cells were used for immunoprecipitations using normal mouse serum, M73 against E1A and 12CA5 against the HA-tag. To check the expression of E1A, HA-BS69 and HA-ΔBS transfected cells were used for immunoprecipitations with M73 and 12CA5. Co-transfected cells with E1A and HA-BS69 or HA-ΔBS were both used for immunoprecipitations with M73 and 12CA5. In transiently transfected U2-OS cells, HA-ΔBS expression vector directed the synthesis of an approximately 50 kDa protein. This protein did not co-immunoprecipitate with E1A whereas wild type BS69 did even though both proteins were equally expressed. One can conclude from these experiments that BS69 interacts with E1A in transiently transfected U2-OS cells, but that a deletion mutant, lacking amino acids 412-562 (HA-ΔBS), fails to interact with E1A.

BS69 interacts with E1A in transformed cells

To detect endogenous BS69 protein, both monoclonal antibodies and rabbit polyclonal antisera were generated against E. coli and baculovirus-produced GST-BS69 fusion protein, respectively. To test the specificity of these antibodies, a line of NIH3T3 cells (3T3 B5) was generated that stably expressed HA-tagged BS69 protein. The polyclonal rabbit BS69 serum was used to immunoprecipitate HA-BS69 from lysates of NIH3T3-B5 cells and endogenous BS69 protein from CAMA human breast carcinoma cells. Subsequently, western blot analysis was performed on these immunoprecipitates using the BS69 monoclonal antibody RK115.

An immunoblot using NIH3T3-B5 cells that stably express HA-BS69 protein and human CAMA breast carcinoma cells was performed. Immunoprecipitations were performed using polyclonal rabbit serum directed against BS69 and normal rabbit serum. Immunoblotting was performed using monoclonal antibody ascites (RK115). The polyclonal rabbit BS69 serum, but not the normal rabbit serum control, immunoprecipitated a protein of approximately 71 kDa in NIH3T3-B5 cells and also the endogenous BS69 protein in CAMA cells. Endogenous BS69 is approximately 2 kDa smaller in molecular weight as compared to the HA-BS69 because it lacks the HA-tag.

To investigate whether endogenous BS69 is complexed with E1A in adenovirus transformed cells, adenovirus 5-transformed human 293 cells was labelled with [$^{32}$P]-orthophosphate. Non-ionic detergent lysates were immunoprecipitated with either normal rabbit serum or with the rabbit polyclonal BS69 serum. Proteins bound to BS69 were released in SDS-containing buffer and re-immunoprecipitated with E1A specific antibody. Again only the largest E1A species was co-immunoprecipitated with BS69 serum whereas both the 243R and 289R E1A protein species are expressed in 293 cells. Taken together, the data indicate that BS69 binds specifically to the large (289R) E1A protein in vivo.

Inhibition of E1A transactivation by BS69

Since BS69 binds to the transactivation domain of 289R E1A whether E1A transactivation was affected by BS69 binding was investigated. 289R E1A was linked to the DNA binding region of the yeast transcription factor GAL4. Transactivation by E1A was measured using a CAT reporter plasmid harboring five GAL4 sites upstream of a core promoter (Lillie and Green, 1989) in a transient transfection in U2-OS cells. FIG. 2A shows that transactivation by GAL4-E1A is dramatically repressed following co-transfection of BS69 expression vector in a concentration-dependent manner. Significantly, other transactivators like GAL4-VP16 and GAL4-E2F-1 were not inhibited by BS69 (FIG. 2B and C). A fusion between GAL4 and the 243R E1A protein also has transactivation ability in U2-OS cells, which is at least 5-fold less compared to 289R E1A. However, transactivation by GAL4-243R E1A was not inhibited by BS69 (FIG. 2D). To investigate whether the interaction of BS69 with CR3 alone resulted in repression, CR3 of 289R E1A was fused to the DNA binding domain of GAL4. It was found that GAL4-CR3 also transactivated the GAL4 reporter gene, albeit at a 10-fold lower level as compared to 289R E1A. Significantly, GAL4-CR3 transactivation was also strongly repressed by BS69 (FIG. 2D).

Figure 2E:
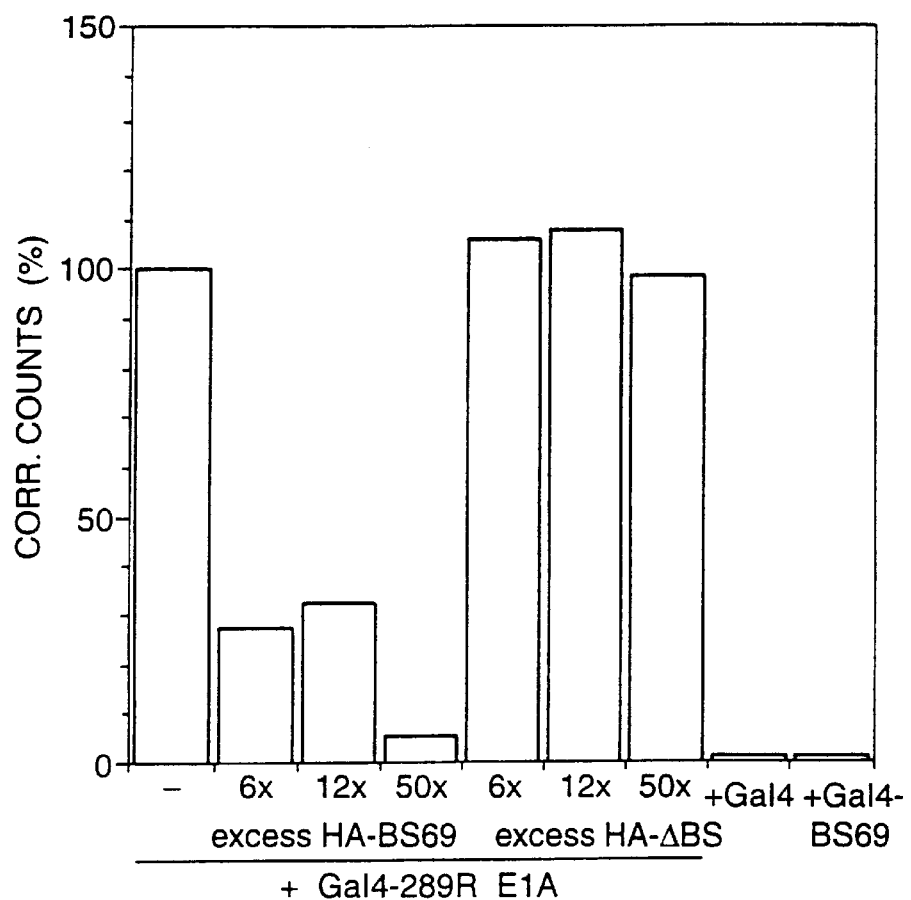

Next it was investigated whether the putative E1A-binding region on BS69 is required to suppress E1A transactivation. The deletion mutant HA-ΔBS was used (FIG. 1), which was unable to bind E1A both in vitro and in vivo. Co-transfection of HA-ΔBS and the GAL4-E1A construct did not result in inhibition of transactivation (FIG. 2E).

It is a formal possibility that BS69 itself is a strong activator of transcription, which "squelches" E1A transactivation when it is highly expressed. FIG. 2E shows that the DNA binding domain of GAL4 does not transactivate in this assay and importantly that a GAL4-BS69 fusion protein also does not transactivate, even though both proteins are highly expressed. This indicates that BS69 has no transactivation ability and suggests that the effect of BS69 on E1A is not the result of squelching. One can conclude from these CAT assays that the effect of BS69 on E1A-mediated transactivation is the result of direct binding of BS69 to the E1A transactivation domain. This interaction with CR3 of E1A requires a region in the carboxyl-terminal 150 amino acids of BS69.

BS69 inhibits the effect of E1A on RAR-dependent transactivation

It has been reported that retinoic acid (RA) signalling by the RAR/RXR complex on the RARb2 promoter can occur via two distinct pathways. The "default" pathway utilized in differentiated cells such as COS-7 and the "superactivation" pathway first observed in Embryonic Carcinoma (EC) cells. RA signalling occurs in EC cells via a cell specific E1A-like activity (E1A-LA) giving rise to superactivation of the RARb2 promoter, and this effect can be mediated in differentiated cells via the adenoviral 289R E1A protein (Berkenstam et al., 1992; Keaveney et al., 1993).

Figure 3A:
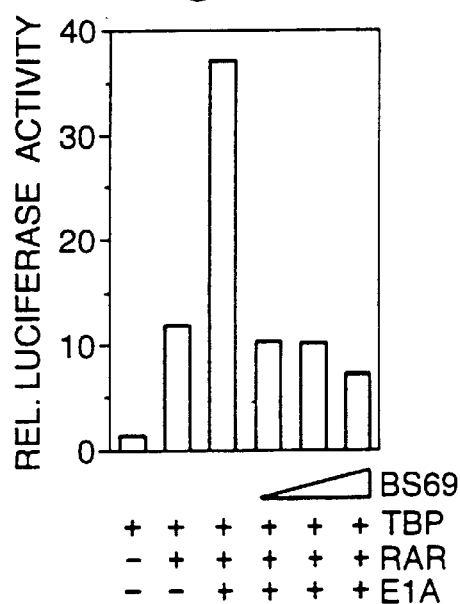

It was therefore tested whether BS69 was able to neutralize the 289R E1A- and the E1A-LA-dependent activation. As shown in FIG. 3A, cotransfection of 289R E1A together with RARb and TBP/spm3 expression vectors resulted in an increased level of transcription from a RARb2 promoter-derived reporter (M1-luc) in COS-7 cells as compared to the activation obtained with RARb and TBP/spm3 alone. Cotransfection of HA-BS69 abolished the 289R E1A-dependent activation, but did not significantly affect the level of transcription from the RARb2 promoter via the default pathway in the absence of 289R E1A. Similarly, 289R E1A-stimulated transcription of the adenoviral E3 promoter was abolished upon cotransfection of HA-BS69, whereas the adenoviral E2 promoter was unaffected by BS69 expression.

Figure 3B:
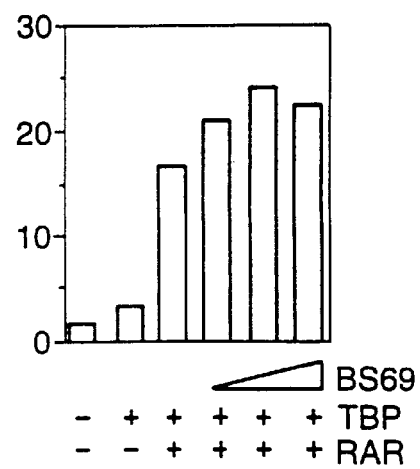

BS69 did not affect the E1A-LA-dependent transactivation of the RARb2 promoter in RAC65 EC cells (FIG. 3B). These results indicate that BS69 can interfere with the E1A effect on RAR-mediated transactivation, but not with the effect of the E1A-LA. These experiments indicate that BS69 is a novel and specific suppressor of transactivation that acts through direct binding to the E1A transactivation domain.

Discussion

An adenovirus E1A protein probe has been used to isolate a cDNA for a novel E1A-interacting protein that has been named BS69. Using specific BS69 antiserum, it was shown that in adenovirus-transformed 293 cells E1A protein is associated with endogenous BS69, indicating that BS69 is a genuine E1A-interacting protein.

A number of cellular polypeptides have been found to co-immunoprecipitate with E1A in adenovirus-infected or -transformed cells (Egan et al., 1987; Harlow et al., 1986; Yee and Branton, 1985). Some of these proteins have now been isolated by molecular cloning. However, cDNAs for a number of these cellular proteins have not yet been isolated.

Egan et al. (1987) have shown that two cellular proteins, p68 and p65, bind very efficiently to *E. coli*-produced E1A proteins. Yee and Branton (1985) also detected a protein of 68 kDa in complex with E1A in adenovirus-infected KB cells. Interestingly, the large E1A protein (289R) bound the 68 kDa cellular protein significantly better than the smaller (243R) E1A protein (Egan et al., 1987; Yee and Branton, 1985). In this respect BS69 resembles the 68 kDa cellular polypeptide, as BS69 also preferentially binds 289R E1A and has lower, but detectable affinity for 243R E1A. It remains to be determined whether p68 is identical to BS69.

BS69 has no known homology to known proteins. The only distinctive features of BS69 are the putative zinc fingers in the amino terminus and the nuclear localization signal. Consistent with this, it was found that BS69 is expressed primarily in the nucleus of transiently transfected cells.

The E1A binding site on BS69 was mapped to the carboxyl-terminal 150 amino acids of BS69. Significantly, the carboxyl-terminal 215 amino acids of human and mouse BS69 are 94% identical, indicating that this motif is highly conserved in evolution. It was found that BS69 binds two independent regions on Ad5 E1A, one located between CR1 and CR2 (residues 76–120) which is a region present in both 243R and 289R E1A proteins. No important functions of E1A have yet been ascribed to this domain of Ad5 E1A.

A second BS69 interaction domain overlaps CR3, the 46 amino acid region that is unique in the 289R E1A protein. CR3 has been the subject of intense study over the last decade and is involved in E1A-mediated transactivation (Martin et al., 1990, Green et al., 1988, Lillie et al., 1987). The data indicates that BS69 strongly and specifically inhibits transactivation by CR3 of 289R E1A. Since BS69 was cloned based on the high affinity of bacterially expressed E1A and *E. coli*-produced BS69, inhibition of E1A transactivation by BS69 is most likely due to a direct interaction of BS69 with residues 76–120 and CR3 of 289R E1A.

These experiments add BS69 to the short list of cellular polypeptides that have the ability to bind and suppress the transactivation domain of transcription factors. The best-characterized in this category of proteins is the retinoblastoma protein. pRb can bind to the transactivation domain of E2F-1, resulting in inhibition of E2F transactivation (Bagchi et al., 1990). Similarly, the pRb-related p107 can bind to the transactivation domain of E2F4 and of c-Myc, in each case causing a dramatic decrease in transactivation (Beijersbergen et al., 1994a and b) and MDM-2 which can suppress p53 transactivation (Oliner et al., 1993). CR3 of 289R E1A is not strictly required for transformation by E1A (Moran et al., 1986). It is therefore unlikely that BS69, like pRb and p107, is a protein with growth inhibitory activity. Consistent with this, an inhibitory effect of BS69 was not observed on the E1A-mediated transformation of rat embryo fibroblasts or baby rat kidney cells. However, since 289R E1A is required for the efficient activation of the other early viral transcription units, BS69 might be able to suppress adenovirus replication in infected cells.

At present it is not clear how BS69 inhibits CR3-dependent transactivation. CR3 has been shown to contain at least two functional domains. One is required for binding to TBP and a more carboxyl-terminal epitope is required for binding to ATF2 (Geisberg et al., 1994). The finding that BS69 binds directly to CR3 and inhibits CR3-mediated transactivation suggests that BS69 might compete with TBP for binding to CR3. A more detailed analysis of the precise epitope in CR3 that is required for BS69 binding should allow further testing of this hypothesis.

In COS cells, the E1A-stimulated transcription of RAR was significantly diminished by BS69. Berkenstam et al. (1992) have suggested that E1A mimics an E1A-like activity (E1A-LA) found in RAC65 EC cells which supports RA dependent transactivation via the superactivation pathway. The data presented here show that ectopic expression of BS69 can inhibit the E1A-stimulated transcription of the retinoic acid receptor in COS-7 cells, but cannot inhibit the E1A-LA in RAC65 cells. Taken together, these results suggest strongly that transactivation by E1A in COS-7 cells is mechanistically different from the transactivation by the E1A-LA in EC cells and that BS69 cannot affect the E1A-LA, although it cannot be excluded that the expression of BS69 in this experiment was at too low a level to observe an effect.

The data also show that BS69 can inhibit E1A transactivation. However, since one does not know the normal function of BS69 in non-adenovirus infected cells, one cannot investigate at present whether E1A also interferes with BS69 function, e.g. by competition with cellular polypeptides for BS69 binding. The yeast two hybrid cloning system has been used to isolate cellular polypeptides that interact with the E1A-binding domain of BS69. A further study of these proteins may help in the elucidation of the normal cellular function of BS69 and the effect of E1A on BS69 function.

REFERENCES

Bagchi, S., Raychaudhuri, P. and Nevins, J. R. (1990) Adenovirus E1A proteins can dissociate heterotrimeric complexes involving the E2F transcription factor: a novel mechanism for E1A transactivation. *Cell,* 62, 659–669.

Bandara, L. R. and La Thangue, N. B. (1991) Adenovirus E1a prevents the retinoblastoma gene product from complexing with a cellular transcription factor. *Nature,* 351, 494–497.

Barbeau, D., Charbomeau, R., Whalen, S. G., Bayley, S. T. and Branton, P. (1994) Functional interactions within adenovirus E1A protein complexes. *Oncogene,* 9, 359–373.

Berkenstam, A., Del Mar Vivanco Ruiz, M., Barettino, D., Horikoshi, M. and Stunnenberg, H. G. (1992) Cooperativity in transactivation between retinoic acid receptor and TFIID requires an activity analogous to E1A. *Cell,* 69, 401–412.

Bernards, R., Houweling, A., Schrier, P. I., Bos, J. L. and Van der Eb, A. J. (1982) Characterization of cells transformed by Ad5/Ad12 hybrid Early region 1 plasmids. *Virology,* 120, 422–432.

Beijersbergen, R. L., Kerkhoven, R. M., Zhu, L., Carlée, L., Voorhoeve, P. M. and Bernards, R. (1994a) E2F-4, a new member of the E2F gene family, has oncogenic activity and associates with p107 in vivo. *Genes Dev.,* 8, 2680–2690.

Beijersbergen, R. L., Hijmans, E. M., Zhu, L. and Bernards, R. (1994b) Interaction of c-Myc with the pRb-related protein p107 results in inhibition of c-Myc-mediated transactivation. *EMBO J.,* 13, 4080–4086.

Borelli, E., Hen, R. and Chambon, P. (1984) Adenovirus-2 E1A products repress enhancer-induced stimulation of transcription. *Nature,* 312, 608–612.

Eckner, R., Ewen, M. E., Newsome, D., Gerdes, M., DeCaprio, J. A., Bentley Lawrence, J. and Livingston, D. M. (1994) Molecular cloning and functional analysis of the adenovirus E1A-associated 300 kD protein (p300) reveals a protein with properties of a transcriptional adaptor. *Genes Dev.,* 8, 869–884.

Egan, C., Yee, S. -P., Ferguson, B., Rosenberg, M. and Branton, P. E. (1987) Binding of cellular polypeptides to human adenovirus type 5 E1A proteins produced in *Escherichia coli. Virology,* 160, 292–296.

Field, J., Nikawa, J., Broek, D., MacDonald, B., Rodgers, L., Wilson, I., Lerner, R. and Wigler, M. (1988) Purification of a RAS-responsive adenylyl cyclase complex from *Saccharomyces cerevisiae* by use of an epitope addition method. *Mol. Cell. Biol.,* 8, 2159–2165.

Geisberg, J. V., Lee, W. S., Berk, A. J. and Ricciardi, R. P. (1994) The zinc finger region of the adenovirus E1A transactivating domain complexes with the TATA box binding protein. *Proc. Natl. Acad. Sci. USA,* 91, 2488–2492.

Green, M., Loewenstein, P. M., Pusztai, R. and Symington, J. S. (1988) An adenovirus E1A protein domain activates transcription in vivo and in vitro in the absence of protein synthesis. *Cell,* 53, 921–926.

Hannon, G. J., Demetrich, D. and Beach, D. (1993) Isolation of the Rb-related p130 through its interaction with cdk2 and cyclins. *Genes Dev.,* 7, 2378–2391.

Harlow, E., Whyte, P., Franza, B. R. and Schley, C. (1986) Association of adenovirus early-region 1A proteins with cellular polypeptides. *Mol. Cell. Biol.,* 6, 1579–1589.

Hateboer, G., Timmers, H. T. M., Rustgi, A. K., Billaud, M., Van 't Veer, L. J. and Bernards, R. (1993) TATA-binding protein and the retinoblastoma gene product bind to overlapping epitopes on c-Nyc and adenovirus E1A protein. *Proc. Natl. Acad. Sci. USA.* 90, 8489–8493.

Horikoshi, N., Maguire, K., Kralli, A., Maldonado, E., Reinberg, D. and Weinmann, R. (1991). Direct interaction between adenovirus E1A protein and the TATA box binding transcription factor IID. *Proc. Natl. Acad. Sci. USA,* 88, 5124–5128.

Houweling, A., Van den Elsen, P. J., and Van der Eb, A. J. (1980) Partial transformation of primary rat cells by the leftmost 4.5% fragment of adenovirus 5 DNA. *Virology,* 105, 537–550.

Howe, J. A., and Bayley, S. T. (1992) Effects of Ad5 E1A mutant viruses on the cell cycle in relation to the binding of cellular proteins including the retinoblastoma protein and cyclin A. *Virology,* 186, 15–24.

Imperiale, M. J., Kao, H. -T., Feldman, L. T., Nevins, J. R. and Strickland, S.(1984) Common control of the heat shock gene and early adenovirus genes: evidence for a cellular E1A-like activity. *Mol. Cell. Biol.,* 4, 867–874.

Jones, N. and Shenk, T. (1979) An adenovirus type 5 early gene function regulates expression of other early viral genes. *Proc. Natl. Acad. Sci. USA,* 76, 3665–3669.

Kaelin, W. G., Krek, W., Sellers, W. R., DeCaprio, J. A., Ajchenbaum, F., Fuchs, C. S., Chittenden, T., Li, Y., Farnham, P., Blanar, M. A., Livingston, D. M. and Flemington, E. K. (1992) Expression cloning of a cDNA encoding a retinoblastoma-binding protein with E2F-like properties. *Cell,* 70, 351–364.

Kato, G. J., Barrett, J., Villa-Garcia, M. and Dang, C. V. (1990) An amino-terminal c-Myc domain required for neoplastic transformation activates transcription. *Mol. Cell. Biol.,* 10, 5914–5920.

Keaveney, M., Berkenstam, A., Feigenbutz, M., Vriend, G. and Stunenberg, H. G. (1993). Residues in the TATA-binding protein required to mediate a transcriptional response to retinoic acid in EC cells. *Nature,* 365, 562–565.

Lee, W. S, Cheng Kao, C., Bryant, G. O., Liu, X. and Berk, A. J. (1991) Adenovirus E1A activation domain binds the basic repeat in the TATA box transcription factor. *Cell,* 67, 365–376.

Li, Y., Graham, C., Lacy, C., Duncan, A. M. V. and Whyte, P. (1993) The adenovirus E1A-associated 130-kD protein is encoded by a member of the retinoblastoma gene family and physically interacts with cyclin A and E. *Genes Dev.,* 7, 2366–2377.

Lillie, J. W., Loewenstein, P. M., Green, M. R. and Green, M. (1987) Functional domains of adenovirus type 5 E1a proteins. *Cell,* 50, 1091–1100.

Lillie, J. W. and Green, M. R. (1989) Transcription activation by the adenovirus E1a protein. *Nature,* 338, 39–44.

Liu, F. and Green, M. R. (1990) A specific member of the ATF transcription factor family can mediate transcription activation by the adenovirus E1a protein. *Cell,* 61, 1217–1224.

Liu, F. and Green, M. R. (1994) Promoter targeting by adenovirus E1a through interaction with different cellular DNA-binding domains. *Nature,* 368, 520–525.

Maguire, K., Shi, X. -P., Horikoshi, N., Rappaport, J., Rosenberg, M. and Weinmann, R. (1991) Interactions between adenovirus E1A and members of the AP-1 family of cellular transcription factors. *Oncogene,* 6, 1417–1422.

Martin, K. J., Lillie, J. W. and Green, M. R. (1990) Evidence for interactions of different eukaryotic transcriptional activators with distinct cellular targets. *Nature,* 346, 147–152.

Mizushima, S. and Nagata, S. (1990) pEF-BOS, a powerful mammalian expression vector. *Nucleic Acids Res.,* 18, 5322.

Momand, J., Zambetti, G. P., Olson, D. C., George, D. and Levine, A. J. (1992) The MDM-2 oncogene product forms a complex with the p53 protein and inhibits p53-mediated transactivation. *Cell,* 69, 1237–1245.

Moran, E., Grodzicker, T., Roberts, R. J., Mathews, M. B. and Zerler, B. (1986) Lytic and transforming functions of individual products of the adenovirus E1A gene. *J. Virol.,* 57, 765–775.

Mymryk, J. S. and Bayley, S. T. (1993) Induction of gene expression by exon 2 of the major E1A proteins of adenovirus type 5. *J. Virol.,* 67, 6922–6928.

Oliner, J. D., Pietenpol, J. A., Thiagalingam, S., Gyuris, J., Kinzler, K. W. and Vogelstein, B. (1993) Oncoprotein MDM2 conceals the activation domain of tumour supressor p53. *Nature,* 362, 857–860.

Pines, J. and Hunter, T. (1990) Human cyclin A is the E1A-associated protein p60 and behaves differently from cyclin B. *Nature,* 346, 760–763.

Seed, B. and Sheen, J. Y. (1988) A simple phase-extraction assay for chloramphenicol acyltransferase activity. *Gene,* 67, 271–277.

Shenk, T. and Flint, J. (1991) Transcriptional and transforming activities of the adenovirus E1A proteins. *Adv. Cancer Res.,* 57, 47–85.

Simon, M. C., Kitchener, K., Kao, H. -T., Hickey, E., Weber, L., Voellmy, R., Heintz, N. and Nevins, J. R. (1987) Selective induction of human heat shock gene transcription by the adenovirus E1A gene products, including the 12S E1A product. *Mol. Cell. Biol.,* 7, 2884–2890.

Stringer, K. F., Ingles, C. J. and Greenblatt, J. (1990) Direct and selective binding of an acidic transcriptional activation domain to the TATA-box factor TFIID. *Nature,* 345, 783–786.

Strubin, M. and Struhl, K. (1992) Yeast and human TFIID with altered DNA-binding specificity for TATA elements. *Cell*, 68, 721–730.

Velcich, A. and Ziff, E. (1985) Adenovirus E1a proteins repress transcription from the SV40 early promoter. *Cell*, 40, 705–716.

Wang, H. -G. H., Draetta, G. and Moran, E. (1991) E1A induces phosphorylation of the retinoblastoma protein independently of direct physical association between the E1A and retinoblastoma products. *Mol. Cell. Biol.*, 11, 4253–4265.

Wang, H. -G. H., Rikitake, Y., Corrigan Carter, M., Yaciuk, P., Abraham, S. E., Zerler, B. and Moran, E. (1993) Identification of specific adenovirus E1A N-terminal residues critical to the binding of cellular proteins and to the control of cell growth. *J. Virol.*, 67, 476–488.

Webster, L. C. and Ricciardi, R. P. (1991) Trans-dominant mutants of E1A provide genetic evidence that the zinc finger of the trans-activating domain binds a transcription factor. *Mol. Cell. Biol.*, 11, 4287–4296.

Whyte, P., Buchkovich, K. J., Horowitz, J. M., Friend, S. F., Raybuck, M., Weinberg, R. A. and Harlow, E. (1988) Association between an oncogene and an anti-oncogene: the adenovinis E1A proteins bind to the retinoblastoma gene product. *Nature*, 334, 124–129.

Whyte, P., Williamson, N. M. and Harlow, E. (1989) Cellular targets for transformation by the adenovirus E1A proteins. *Cell*, 56, 67–75.

Yee, S. -P., and Branton, P. E. (1985) Detection of cellular proteins associated with human adenovirus type 5 early region 1A polypeptides. *Virology*, 147, 142–153.

Zhu, L., Van den Heuvel, S., Helin, K., Fattaey, A., Ewen, M., Livingston, D., Dyson, N. and Harlow, E. (1993) Inhibition of cell prolifiration by p107, a relative of the retinoblastoma protein. *Genes Dev.*, 7, 1111–1125.

We claim:

1. An isolated polynucleotide which comprises the sequence of nucleotides shown in SEQ ID NO:1 or which is capable of encoding a polypeptide that comprises:
   (a) the protein shown in SEQ ID NO:2 or
   (b) a fragment of the protein shown in SEQ ID NO:2, which fragment comprises the E1A binding region located in residues 412–532 of SEQ ID NO:2 and which is capable of binding to the adenovirus E1A 289R or 243R protein.

2. An isolated polynucleotide according to claim 1 which is a DNA polynucleotide.

3. An isolated polynucleotide according to claim 1 which comprises the cDNA sequence shown in SEQ. ID NO: 1.

4. A double stranded polynucleotide comprising a polynucleotide according to claim 1 and its complementary sequence.

5. A polynucleotide according to claim 4 carrying a revealing or detectable label.

6. A vector comprising a polynucleotide according to claim 5.

7. The polynucleotide according to claim 1 wherein said polynucleotide encodes the protein shown in SEQ ID NO:2.

8. A recombinant replicable vector comprising a coding sequence which encodes a polypeptide comprising:
   (a) the protein shown in SEQ ID NO:2 or
   (b) a fragment of the protein shown in SEQ ID NO:2, which fragment comprises the E1A binding region located in residues 412–532 of SEQ ID NO:2 and which is capable of binding to the adenovirus E1A 289R or 243R protein,
   wherein said coding sequence is operably linked to a promoter.

9. The recombinant vector according to claim 8, wherein the coding sequence encodes the protein shown in SEQ ID NO:2.

10. A host cell comprising a vector according to claim 8.

11. A process for preparing a polypeptide, the process comprising cultivating a host cell according to claim 10 under conditions providing for expression of the recombinant vector of the coding sequence, and recovering the expressed polypeptide.

12. The process according to claim 11 wherein the polypeptide is the protein shown in SEQ ID NO:2.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2623 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION:150..1835

(xi) SEQUENCE DESCRIPTION: SEQ ID NO: 1:

```
GGAGCATAAT GCTAAAGAAG TAAACAGGTC ATGGCACGTT TAACAAAAAG ACGACAGGCG        60

ATACAAAAGC TATCCAGCAT CTTTGGGCAG CCATTGAGAT TATACGGAAC CAGAAGCAGA       120

TTGCCAACAT TGACCGTATT ACAAAGTAT ATG TCT CGA GTC CAC GGT ATG CAC        173
                                Met Ser Arg Val His Gly Met His
                                  1               5

CCT AAA GAG ACC ACC CGT CAG CTG AGC TTA GCT GTG AAA GAT GGT CTT        221
Pro Lys Glu Thr Thr Arg Gln Leu Ser Leu Ala Val Lys Asp Gly Leu
    10                  15                  20

ATT GTC GAA ACT CTA ACA GTG GGC TGC AAA GGT TCA AAA GCT GGT ATT        269
Ile Val Glu Thr Leu Thr Val Gly Cys Lys Gly Ser Lys Ala Gly Ile
25                  30                  35                  40

GAA CAA GAA GGA TAT TGG TTG CCA GGA GAT GAG ATT GAC TGG GAA ACA        317
Glu Gln Glu Gly Tyr Trp Leu Pro Gly Asp Glu Ile Asp Trp Glu Thr
                45                  50                  55

GAA AAT CAT GAC TGG TAT TGT TTT GAA TGC CAT TTG CCT GGA GAG GTG        365
Glu Asn His Asp Trp Tyr Cys Phe Glu Cys His Leu Pro Gly Glu Val
             60                  65                  70

TTG ATA TGT GAC CTG TGT TTT CGT GTG TAT CAT TCC AAG TGT TTG TCT        413
Leu Ile Cys Asp Leu Cys Phe Arg Val Tyr His Ser Lys Cys Leu Ser
         75                  80                  85

GAT GAG TTC AGG CTT AGA GAC AGC AGT AGT CCC TGG CAG TGC CCA GTT        461
Asp Glu Phe Arg Leu Arg Asp Ser Ser Ser Pro Trp Gln Cys Pro Val
     90                  95                 100

TGC AGG AGC ATT AAG AAG AAG AAT ACA AAC AAA CAG GAG ATG GGC ACA        509
```

|     |     |     |     |     |     |     |     |     |     |     |     |     |     |     |     |
| --- | --- | --- | --- | --- | --- | --- | --- | --- | --- | --- | --- | --- | --- | --- | --- |
| Cys | Arg | Ser | Ile | Lys | Lys | Lys | Asn | Thr | Asn | Lys | Gln | Glu | Met | Gly | Thr |
| 105 |     |     |     | 110 |     |     |     |     | 115 |     |     |     |     | 120 |     |

```
TAC CTC AGA TTC ATT GTC TCC CGC ATG AAG GAG AGG GCT ATA GAT CTT      557
Tyr Leu Arg Phe Ile Val Ser Arg Met Lys Glu Arg Ala Ile Asp Leu
            125                 130                 135

AAT AAA AAG GGG AAG GAC AAT AAA CAC CCG ATG TAC AGG AGG CTG GTG      605
Asn Lys Lys Gly Lys Asp Asn Lys His Pro Met Tyr Arg Arg Leu Val
            140                 145                 150

CAC TCA GCT GTG GAC GTT CCC ACC ATT CAA GAG AAA GTG AAT GAA GGG      653
His Ser Ala Val Asp Val Pro Thr Ile Gln Glu Lys Val Asn Glu Gly
            155                 160                 165

AAA TAC CGA AGT TAT GAA GAG TTC AAA GCT GAT GCC CAA TTG CTT CTC      701
Lys Tyr Arg Ser Tyr Glu Glu Phe Lys Ala Asp Ala Gln Leu Leu Leu
    170                 175                 180

CAC AAT ACC GTG ATT TTC TAT GGA GCA GAC AGT GAG CAA GCT GAC ATT      749
His Asn Thr Val Ile Phe Tyr Gly Ala Asp Ser Glu Gln Ala Asp Ile
185                 190                 195                 200

GCG AGG ATG CTA TAT AAA GAC ACA TGT CAT GAG CTG GAT GAA CTG CAG      797
Ala Arg Met Leu Tyr Lys Asp Thr Cys His Glu Leu Asp Glu Leu Gln
                205                 210                 215

CTT TGC AAG AAT TGC TTT TAC TTG TCA AAT GCT CGT CCT GAC AAC TGG      845
Leu Cys Lys Asn Cys Phe Tyr Leu Ser Asn Ala Arg Pro Asp Asn Trp
                220                 225                 230

TTC TGT TAT CCT TGT ATA CCT AAT CAT GAG CTG GTT TGG GCT AAA ATG      893
Phe Cys Tyr Pro Cys Ile Pro Asn His Glu Leu Val Trp Ala Lys Met
            235                 240                 245

AAA GGT TTT GGG TTT TGG CCA GCC AAA GTC ATG CAG AAA GAA GAC AAT      941
Lys Gly Phe Gly Phe Trp Pro Ala Lys Val Met Gln Lys Glu Asp Asn
    250                 255                 260

CAA GTC GAC GTT CGC TTC TTT GGC CAC CAC CAC CAG AGG GCC TGG ATT      989
Gln Val Asp Val Arg Phe Phe Gly His His His Gln Arg Ala Trp Ile
265                 270                 275                 280

CCT TCT GAA AAC ATT CAA GAT ATC ACA GTC AAC ATT CAT CGG CTG CAC     1037
Pro Ser Glu Asn Ile Gln Asp Ile Thr Val Asn Ile His Arg Leu His
                285                 290                 295

GTG AAG CGC AGT ATG GGT TGG AAA AAG GCC TGT GAT GAG CTG GAG CTG     1085
Val Lys Arg Ser Met Gly Trp Lys Lys Ala Cys Asp Glu Leu Glu Leu
                300                 305                 310

CAT CAG CGT TTC CTA CGA GAA GGG AGA TTT TGG AAA TCT AAG AAT GAG     1133
His Gln Arg Phe Leu Arg Glu Gly Arg Phe Trp Lys Ser Lys Asn Glu
            315                 320                 325

GAC CGA GGT GAG GAA GAG GCA GAA TCC AGT ATC TCC TCC ACC AGT AAT     1181
Asp Arg Gly Glu Glu Glu Ala Glu Ser Ser Ile Ser Ser Thr Ser Asn
    330                 335                 340

GAG CAG CTA AAG GTC ACT CAA GAA CCA AGA GCA AAG AAA GGA CGA CGT     1229
Glu Gln Leu Lys Val Thr Gln Glu Pro Arg Ala Lys Lys Gly Arg Arg
345                 350                 355                 360

AAT CAA AGT GTG GAG CCC AAA AAG GAA GAA CCA GAG CCT GAA ACA GAA     1277
Asn Gln Ser Val Glu Pro Lys Lys Glu Glu Pro Glu Pro Glu Thr Glu
                365                 370                 375

GCA GTA AGT TCT AGC CAG GAA ATA CCC ACG ATG CCT CAG CCC ATC GAA     1325
Ala Val Ser Ser Ser Gln Glu Ile Pro Thr Met Pro Gln Pro Ile Glu
                380                 385                 390

AAA GTC TCC GTG TCA ACT CAG ACA AAG AAG TTA AGT GCC TCT TCA CCA     1373
Lys Val Ser Val Ser Thr Gln Thr Lys Lys Leu Ser Ala Ser Ser Pro
            395                 400                 405

AGA ATG CTG CAT CGG AGC ACC CAG ACC ACA AAC GAC GGC GTG TGT CAG     1421
Arg Met Leu His Arg Ser Thr Gln Thr Thr Asn Asp Gly Val Cys Gln
    410                 415                 420

AGC ATG TGC CAT GAC AAA TAC ACC AAG ATC TTC AAT GAC TTC AAA GAC     1469
```

```
Ser Met Cys His Asp Lys Tyr Thr Lys Ile Phe Asn Asp Phe Lys Asp
425                 430                 435                 440

CGG ATG AAG TCG GAC CAC AAG CGG GAG ACA GAG CGT GTT GTC CGA GAA      1517
Arg Met Lys Ser Asp His Lys Arg Glu Thr Glu Arg Val Val Arg Glu
                    445                 450                 455

GCT CTG GAG AAG CTG CGT TCT GAA ATG GAA GAA GAA AAG AGA CAA GCT      1565
Ala Leu Glu Lys Leu Arg Ser Glu Met Glu Glu Glu Lys Arg Gln Ala
            460                 465                 470

GTA AAT AAA GCT GTA GCC AAC ATG CAG GGT GAG ATG GAC AGA AAA TGT      1613
Val Asn Lys Ala Val Ala Asn Met Gln Gly Glu Met Asp Arg Lys Cys
        475                 480                 485

AAG CAA GTA AAG GAA AAG TGT AAG GAG GAA TTT GTA GAA GAA ATC AAG      1661
Lys Gln Val Lys Glu Lys Cys Lys Glu Glu Phe Val Glu Glu Ile Lys
    490                 495                 500

AAG CTG GCA ACA CAG CAC AAG CAA CTG ATT TCT CAG ACC AAG AAG AAG      1709
Lys Leu Ala Thr Gln His Lys Gln Leu Ile Ser Gln Thr Lys Lys Lys
505                 510                 515                 520

CAG TGG TGC TAC AAC TGT GAG GAG GAG GCC ATG TAC CAC TGC TGC TGG      1757
Gln Trp Cys Tyr Asn Cys Glu Glu Glu Ala Met Tyr His Cys Cys Trp
                    525                 530                 535

AAC ACA TCC TAC TGC TCC ATC AAG TGC CAG CAG GAG CAC TGG CAC GCG      1805
Asn Thr Ser Tyr Cys Ser Ile Lys Cys Gln Gln Glu His Trp His Ala
                540                 545                 550

GAG CAC AAG CGC ACC TGC CGC CGG AAA AGA TGAAGCTGGC CCTTCCCGGA        1855
Glu His Lys Arg Thr Cys Arg Arg Lys Arg
            555                 560

GTCACCCCGA TGATTACTCT TTTCAGACAC AGCGGTTTTT GTTTCCAAGA AGCCAAAATT   1915

GTTTAGAATT TGCTTCCCAT TTTGCACCAG CCTTTAAACA CTTTTCGTGA AGAAATTTTG   1975

CACAGTAGTT TAAATCTTTT GTTAATGCTC CTCCGAAGTT TTTCAGGGGG TAAAAGTAAC   2035

ATCAGTGGAG GGTATTATTT TAAATAAATT TTAATTGAGA ATTTGTTGCA TTTTCAGCAA   2095

ATTTTAAAAC ATTTTTAGGT TTTACAGAGA TTTTAACCTT TAAACAACAG ATCTTTAAAA   2155

AACAGGTGAA TACAAGTGAG TTTAACAAAG AAACATTTAG AATAGATCTG AATGTAAGAA   2215

CTACAGAACT GTTTCAGAAA TAAAACATAC TACCTTGATG TGACATTTTT TTCTTAACCT   2275

TGTTGAGCTG GTTTTGTTCA GCTTAATTTA CTGTTCAAAG GCATTATCTG TTGGTCACAC   2335

CAGTGGGTAT ATGATTGAAT TTAGGGAACA GGGTTGACAC AGCAGGGCTA GTCCTGCATA   2395

TTTTTTCTTA ATATTTCCC AATTGTGTTT TTCATTATTT CTTTTCAATA TATAACTTTT    2455

ATAACAAATT ATTAGCTTTG ATCTTGTAGT TTAAAATTGC AGGGAACTGG GGTAATCTTT   2515

TACTGAGCTG GATCTTAGAG AAAATGAATA TTTAAATTTT AAAGTTTGCC ACATTTCATC   2575

TTTGTCCTAA CATGAGTGCT TGTAACAAAA TAAAACAACA AAAACAAA                2623

(2) INFORMATION FOR SEQ ID NO: 2:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO: 2:

Met Ser Arg Val His Gly Met His Pro Lys Glu Thr Thr Arg Gln Leu
1               5                   10                  15

Ser Leu Ala Val Lys Asp Gly Leu Ile Val Glu Thr Leu Thr Val Gly
            20                  25                  30

Cys Lys Gly Ser Lys Ala Gly Ile Glu Gln Glu Gly Tyr Trp Leu Pro
```

```
                35                  40                  45
Gly Asp Glu Ile Asp Trp Glu Thr Glu Asn His Asp Trp Tyr Cys Phe
         50                  55                  60

Glu Cys His Leu Pro Gly Glu Val Leu Ile Cys Asp Leu Cys Phe Arg
 65                  70                  75                  80

Val Tyr His Ser Lys Cys Leu Ser Asp Glu Phe Arg Leu Arg Asp Ser
                 85                  90                  95

Ser Ser Pro Trp Gln Cys Pro Val Cys Arg Ser Ile Lys Lys Lys Asn
             100                 105                 110

Thr Asn Lys Gln Glu Met Gly Thr Tyr Leu Arg Phe Ile Val Ser Arg
         115                 120                 125

Met Lys Glu Arg Ala Ile Asp Leu Asn Lys Lys Gly Lys Asp Asn Lys
     130                 135                 140

His Pro Met Tyr Arg Arg Leu Val His Ser Ala Val Asp Val Pro Thr
145                 150                 155                 160

Ile Gln Glu Lys Val Asn Glu Gly Lys Tyr Arg Ser Tyr Glu Glu Phe
                 165                 170                 175

Lys Ala Asp Ala Gln Leu Leu His Asn Thr Val Ile Phe Tyr Gly
             180                 185                 190

Ala Asp Ser Glu Gln Ala Asp Ile Ala Arg Met Leu Tyr Lys Asp Thr
             195                 200                 205

Cys His Glu Leu Asp Glu Leu Gln Leu Cys Lys Asn Cys Phe Tyr Leu
     210                 215                 220

Ser Asn Ala Arg Pro Asp Asn Trp Phe Cys Tyr Pro Cys Ile Pro Asn
225                 230                 235                 240

His Glu Leu Val Trp Ala Lys Met Lys Gly Phe Gly Phe Trp Pro Ala
                 245                 250                 255

Lys Val Met Gln Lys Glu Asp Asn Gln Val Asp Val Arg Phe Phe Gly
             260                 265                 270

His His His Gln Arg Ala Trp Ile Pro Ser Glu Asn Ile Gln Asp Ile
         275                 280                 285

Thr Val Asn Ile His Arg Leu His Val Lys Arg Ser Met Gly Trp Lys
     290                 295                 300

Lys Ala Cys Asp Glu Leu Glu Leu His Gln Arg Phe Leu Arg Glu Gly
305                 310                 315                 320

Arg Phe Trp Lys Ser Lys Asn Glu Asp Arg Gly Glu Glu Ala Glu
                 325                 330                 335

Ser Ser Ile Ser Ser Thr Ser Asn Glu Gln Leu Lys Val Thr Gln Glu
             340                 345                 350

Pro Arg Ala Lys Lys Gly Arg Arg Asn Gln Ser Val Glu Pro Lys Lys
         355                 360                 365

Glu Glu Pro Glu Pro Glu Thr Glu Ala Val Ser Ser Ser Gln Glu Ile
     370                 375                 380

Pro Thr Met Pro Gln Pro Ile Glu Lys Val Ser Val Ser Thr Gln Thr
385                 390                 395                 400

Lys Lys Leu Ser Ala Ser Ser Pro Arg Met Leu His Arg Ser Thr Gln
                 405                 410                 415

Thr Thr Asn Asp Gly Val Cys Gln Ser Met Cys His Asp Lys Tyr Thr
             420                 425                 430

Lys Ile Phe Asn Asp Phe Lys Asp Arg Met Lys Ser Asp His Lys Arg
         435                 440                 445

Glu Thr Glu Arg Val Val Arg Glu Ala Leu Glu Lys Leu Arg Ser Glu
     450                 455                 460
```

```
Met Glu Glu Glu Lys Arg Gln Ala Val Asn Lys Ala Val Ala Asn Met
465                 470                 475                 480

Gln Gly Glu Met Asp Arg Lys Cys Lys Gln Val Lys Glu Lys Cys Lys
                485                 490                 495

Glu Glu Phe Val Glu Glu Ile Lys Lys Leu Ala Thr Gln His Lys Gln
            500                 505                 510

Leu Ile Ser Gln Thr Lys Lys Lys Gln Trp Cys Tyr Asn Cys Glu Glu
        515                 520                 525

Glu Ala Met Tyr His Cys Cys Trp Asn Thr Ser Tyr Cys Ser Ile Lys
        530                 535                 540

Cys Gln Gln Glu His Trp His Ala Glu His Lys Arg Thr Cys Arg Arg
545                 550                 555                 560

Lys Arg
```